(12) United States Patent
Xu et al.

(10) Patent No.: US 11,124,481 B2
(45) Date of Patent: Sep. 21, 2021

(54) METHOD OF PREPARING FLUORINE-18 LABELED CABOZANTINIB AND ITS ANALOGS

(71) Applicant: Exelixis, Inc., Alameda, CA (US)

(72) Inventors: Wei Xu, Danville, CA (US); David J. Donnelly, Doylestown, PA (US); Patrick L. Chow, Lawrenceville, NJ (US); Benjamin J. Henley, Mount Laurel, NJ (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 15/500,312

(22) PCT Filed: Jul. 31, 2015

(86) PCT No.: PCT/US2015/043195
§ 371 (c)(1),
(2) Date: Jan. 30, 2017

(87) PCT Pub. No.: WO2016/019285
PCT Pub. Date: Feb. 4, 2016

(65) Prior Publication Data
US 2017/0217896 A1 Aug. 3, 2017

Related U.S. Application Data

(60) Provisional application No. 62/031,471, filed on Jul. 31, 2014.

(51) Int. Cl.
*C07D 215/233* (2006.01)
*C07D 215/22* (2006.01)

(52) U.S. Cl.
CPC ....... *C07D 215/233* (2013.01); *C07D 215/22* (2013.01)

(58) Field of Classification Search
CPC .......................... C07D 215/233; C07D 215/22
See application file for complete search history.

(56) References Cited

U.S. PATENT DOCUMENTS

| | | |
|---|---|---|
| 7,579,473 B2 | 8/2009 | Bannen et al. |
| 7,977,345 B2 | 7/2011 | Bannen et al. |
| 7,999,006 B2 | 8/2011 | Lamb |
| 8,067,436 B2 | 11/2011 | Bannen et al. |
| 8,178,532 B2 | 5/2012 | Bannen et al. |
| 8,314,232 B2 | 11/2012 | Deschamps et al. |
| 8,476,298 B2 | 7/2013 | Bannen et al. |
| 8,497,284 B2 | 7/2013 | Bannen et al. |
| 8,673,912 B2 | 3/2014 | Cannon et al. |
| 8,877,776 B2 | 11/2014 | Brown et al. |
| 9,174,947 B2 | 11/2015 | Bannen et al. |
| 9,365,516 B2 | 6/2016 | Wilson et al. |
| 9,717,720 B2 | 8/2017 | Wilson et al. |
| 9,724,342 B2 | 8/2017 | Wilson et al. |
| 9,809,549 B2 | 11/2017 | Brown et al. |
| 9,861,624 B2 | 1/2018 | Aftab et al. |
| 9,969,692 B2 | 5/2018 | Wilson et al. |
| 10,034,873 B2 | 7/2018 | Wilson et al. |
| 10,039,757 B2 | 9/2018 | Wilson et al. |
| 10,159,666 B2 | 12/2018 | Aftab et al. |
| 10,166,225 B2 | 1/2019 | Aftab et al. |
| 10,273,211 B2 | 4/2019 | Aftab et al. |
| 10,501,415 B2 | 12/2019 | Fukubayashi et al. |
| 10,543,206 B2 | 1/2020 | Wilson et al. |
| 10,548,888 B2 | 2/2020 | Wilson et al. |
| 2008/0161305 A1 | 7/2008 | Forsyth et al. |
| 2009/0274693 A1 | 11/2009 | Gilmer et al. |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Kallender et al. |
| 2013/0330377 A1 | 12/2013 | Wilson |
| 2014/0057908 A1 | 2/2014 | Smith et al. |
| 2014/0057943 A1 | 2/2014 | Smith et al. |
| 2014/0066444 A1 | 3/2014 | Smith et al. |

(Continued)

FOREIGN PATENT DOCUMENTS

| | | | |
|---|---|---|---|
| CN | 103664776 | * | 9/2012 |
| CN | 103664776 | | 3/2014 |

(Continued)

OTHER PUBLICATIONS

Haka, et al., "Aryltrimethylammonium trifluoromethanesulfonates as precursors to aryl [18F]Fluorides: improved synthesis of [18F)GBR-13119", Journal of Labelled Compounds and Radiopharmaceuticals, vol. 27, No. 7, pp. 823-833, 1989.

Seimbille, et al., "Flourine-18 labeling of 6,7-disubstituted anilinoquinazoline derivatives for positron emission tomography (PET) imaging of tyrosine kinase receptors: synthesis of 18F-Iressa and related molecular probes", Journal of Labelled Compounds and Radiopharmaceuticals, vol. 44, No. 11, pp. 829-843, 2005.

Monaco et al., "Synthesis and in vitro evaluation of a novel radioligand for avb3 integrin receptor imaging," Bioorganic & Medicinal Chemistry Letters, 23 6068-6072, 2013.

(Continued)

*Primary Examiner* — D Margaret M Seaman
(74) *Attorney, Agent, or Firm* — Honigman LLP; Heidi M. Berven

(57) ABSTRACT

The present invention relates to a method of preparing Cabozantinib (Cyclopropane-1,1-dicarboxylic acid [4-(6,7-dimethoxy-quinolin-4-yloxy)-phenylo]amide(4-fluoro-phenyl)amide) and $^{18}$F labeled Cabozantinib.

21 Claims, 5 Drawing Sheets

(56) References Cited

U.S. PATENT DOCUMENTS

| | | |
|---|---|---|
| 2014/0121239 A1 | 5/2014 | Aftab |
| 2014/0155396 A1 | 6/2014 | Bannen et al. |
| 2014/0179736 A1 | 6/2014 | Schwab et al. |
| 2014/0221372 A1 | 8/2014 | Kulkarni et al. |
| 2014/0228401 A1 | 8/2014 | Aftab et al. |
| 2014/0256938 A1 | 9/2014 | Wilson et al. |
| 2014/0302012 A1 | 10/2014 | Aftab et al. |
| 2014/0323522 A1 | 10/2014 | Aftab et al. |
| 2015/0057310 A1 | 2/2015 | Brown et al. |
| 2015/0133494 A1 | 5/2015 | Aftab et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0022662 A1* | 1/2016 | DeCillis ............... A61K 9/2054 424/465 |
| 2016/0031818 A1* | 2/2016 | Aftab ................... C07D 215/22 514/312 |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0042880 A1 | 2/2017 | Aftab et al. |
| 2017/0044106 A1 | 2/2017 | Aftab et al. |
| 2017/0057921 A1 | 3/2017 | Wilson et al. |
| 2017/0087143 A1* | 3/2017 | Aftab .................... A61K 31/47 |
| 2017/0143689 A1 | 5/2017 | Wilson et al. |
| 2017/0224670 A1 | 8/2017 | Smalley |
| 2017/0224672 A1 | 8/2017 | Aftab et al. |
| 2017/0266178 A1 | 9/2017 | Wilson et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |
| 2018/0311229 A1 | 11/2018 | Wilson et al. |
| 2019/0030021 A1 | 1/2019 | Wilson et al. |
| 2019/0076420 A1* | 3/2019 | Aftab ................... A61K 9/2054 |
| 2019/0091215 A1 | 3/2019 | Aftab et al. |
| 2019/0151302 A1 | 5/2019 | Aftab et al. |
| 2019/0218182 A1 | 7/2019 | Aftab et al. |
| 2019/0352403 A1 | 11/2019 | Schwab et al. |

FOREIGN PATENT DOCUMENTS

| | | |
|---|---|---|
| EP | 2058302 | 5/2009 |
| JP | 2007-056777 | 3/2007 |
| WO | 2005030140 * | 4/2005 |
| WO | 2013043840 A1 | 3/2013 |
| WO | 2014145715 | 9/2014 |

\* cited by examiner

METHOD OF PREPARING FLUORINE-18 LABELED CABOZANTINIB AND ITS ANALOGS

CROSS-REFERENCE TO RELATED APPLICATIONS

This application is a United States National Phase filing of PCT/US2015/043195, filed Jul. 31, 2015, which claims the benefit of U.S. Provisional Application No. 62/031,471, filed Jul. 31, 2014, the entire contents of which are incorporated herein by reference.

FIELD OF THE INVENTION

The present invention relates to a method of preparing Cabozantinib (Cyclopropane-1,1-dicarboxylic acid [4-(6,7-dimethoxy-quinolin-4-yloxy)-phenylo]amide(4-fluoro-phenyl)amide) and $^{18}$F-labeled Cabozantinib.

BACKGROUND OF THE INVENTION

Molecular imaging provides a non-invasive assessment of biological and biochemical processes in living subjects. The use of positron emission tomography (PET) has the potential to enhance the understanding of a potential drug during preclinical and clinical drug development. This information would be especially important in determining whether a potential drug reaches its target tissue in challenging environments such as glioblastoma multiforme (GBM) brain tumors.

Cabozantinib (Cyclopropane-1,1-dicarboxylic acid [4-(6,7-dimethoxy-quinolin-4-yloxy)-phenylo]amide(4-fluoro-phenyl)amide, (1) is a multitargeted kinase inhibitor with inhibitory activity against vascular endothelial growth factor receptor-2 (VEGFR-2) ($IC_{50}$ of 0.035 nM), tyrosine kinase MET ($IC_{50}$ of 1.3 nM), receptor tyrosine kinase encoded by rearranged during transfection (RET) proto-oncogene ($IC_{50}$ 4 nM), and c-KIT (stem-cell factor) ($IC_{50}$ of –4.6 nM).

I

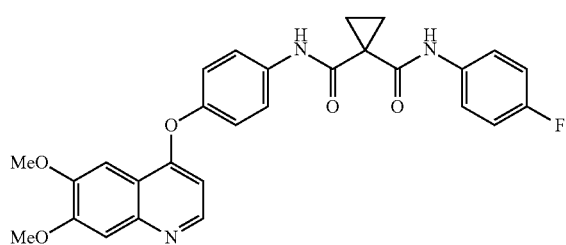

In cellular assays, Cabozantinib inhibits phosphorylation of receptors VEGFR-2, RET, and MET, as well as c-KIT, with $IC_{50}$ values of 1.9, 7.8, 5.0, and 42 nM, respectively. Cabozantinib inhibits MET and VEGFR-2 phosphorylation in tumor models in vivo and demonstrates potent antimetastatic, antitumor, and antiangiogenic activity in preclinical models. The vascular endothelial growth factor (VEGF) and the hepatocyte growth factor (HGF) are potent mediators of angiogenesis. Angiogenesis is the formation of new blood vessels and is one of the key requirements of tumor growth during cancer progression. Recent studies suggest that activation of VEGF through the VEFGR-2 and the HGF receptor kinase MET, play synergistic roles in tumor progression.

In 2012, the FDA approved Cabozantinib as the L-malate salt (COMETRIQ®, Exelixis, Inc.) for the treatment of patients with progressive metastatic medullary thyroid cancer (MTC) and is currently being evaluated in patients with glioblastoma multiforme. Over expression of MET and VEGFR-2 have shown to correlate with poor prognosis in GBM, one of the most common and aggressive brain tumors.

The synthesis of Cabozantinib (1) has been previously described in International Patent Application publication No. WO 2005/030140 filed Sep. 9, 2004, the contents of which are incorporated herein by reference in its entirety. There remains a need for new processes for synthesizing Cabozantinib and isotopically labeled Cabozantinib, [18F]-Cabozantinib, in a minimum number of steps and concomitant high yields.

SUMMARY OF THE INVENTION

These and other needs are met by the present invention which is directed to a method for synthesizing Cabozantinib by incorporating the fluoroaniline moiety as the last step of the synthesis. In some embodiments, 1-(4-(6,7-dimethoxy-quinolin-3-yloxy)phenylcarbamoyl)cyclopropanecarboxylic acid is coupled with 4-fluoroaniline or [18]-fluoroaniline.

Thus, in one aspect, the present invention provides a method for generating a compound of Formula I:

Formula I

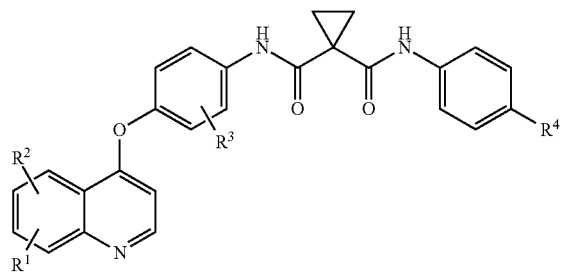

or a pharmaceutically acceptable salt thereof, wherein each of $R^1$ and $R^2$ is independently alkoxy or haloalkoxy; $R^3$ is H, F, Cl, I or Br; and $R^4$ is F, $^{18}$F, Cl, I or Br; comprising:

i) reacting a compound of Formula 8 with a compound of Formula 9 in the presence of a coupling reagent to generate a compound of Formula I:

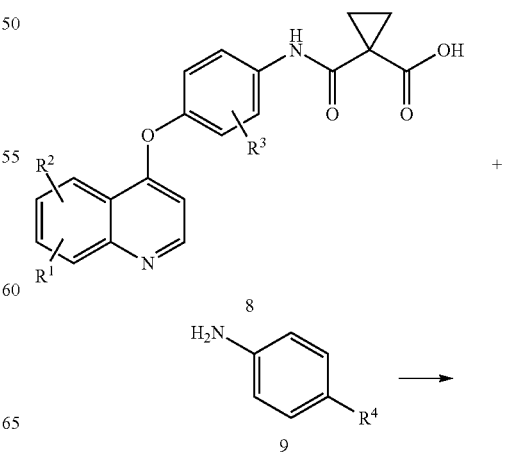

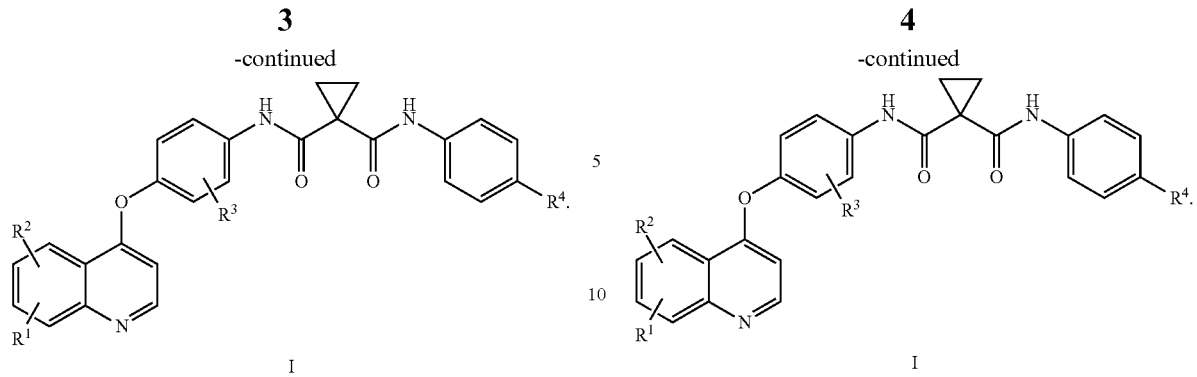

In some implementations, the coupling reagent is selected from the group consisting of N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent), benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-Tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), and (1-cyano-2-ethoxy-2-oxoethylidenaminooxy)dimethylamino-morpholino-carbenium hexafluorophosphate (COMU) or a combination thereof.

Another aspect of the present invention provides a method for generating a compound of Formula I or a pharmaceutically acceptable salt thereof wherein each of $R^1$ and $R^2$ is independently alkoxy or haloalkoxy; $R^3$ is H, F, Cl, I or Br; and $R^4$ is F, $^{18}F$, Cl, I or Br; comprising:

i) reacting a compound of Formula 8 with a compound of Formula 9 in the presence of a coupling reagent and heating the reaction with microwave radiation to generate a compound of Formula I:

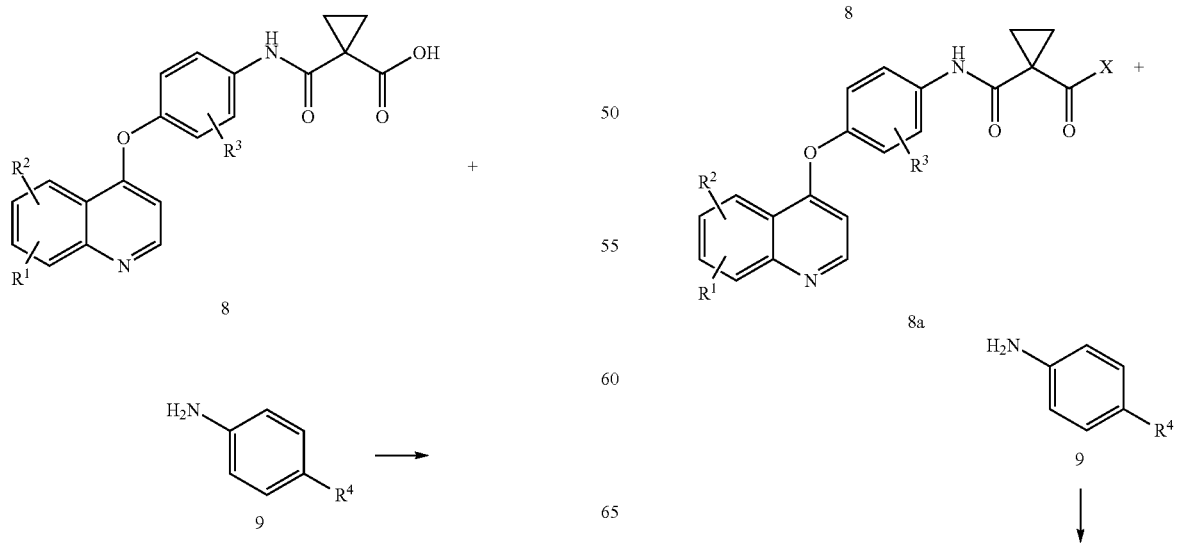

In some embodiments, heating the reaction during the coupling reaction using microwave radiation results in shorter reaction times compared to the coupling reaction without microwave heating. In some embodiments, microwave radiation can be applied to the coupling reaction in an amount ranging from about 10 watts to about 20 watts, thereby generating a higher yield of a compound of Formula I as compared to the yield of a compound of Formula I in the absence of microwave heating.

Another aspect of the present invention provides a method for synthesizing a compound of Formula I, the method comprising:

i) reacting a compound of Formula 8 with a halogenating agent to generate an acid halide compound of Formula 8a, followed by reacting the acid halide compound of Formula 8a with a compound of Formula 9 in the presence of a base to generate the compound of Formula I:

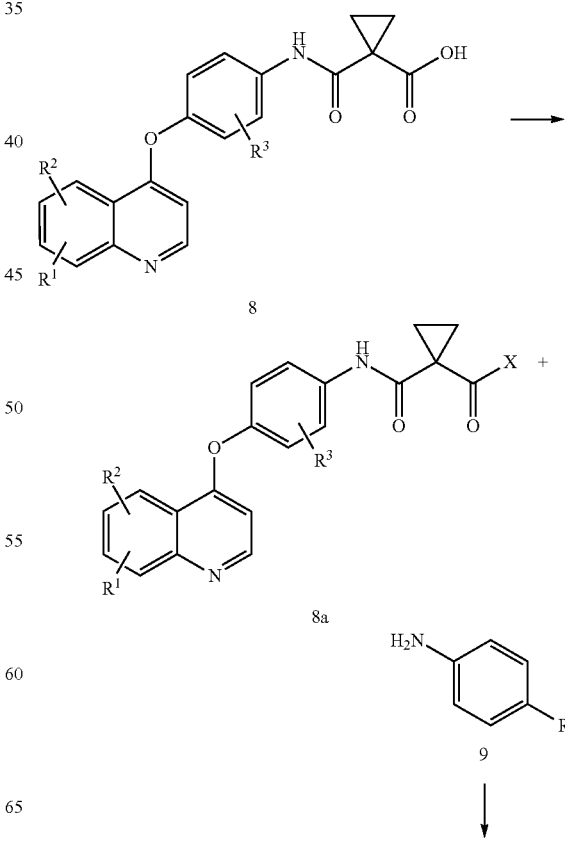

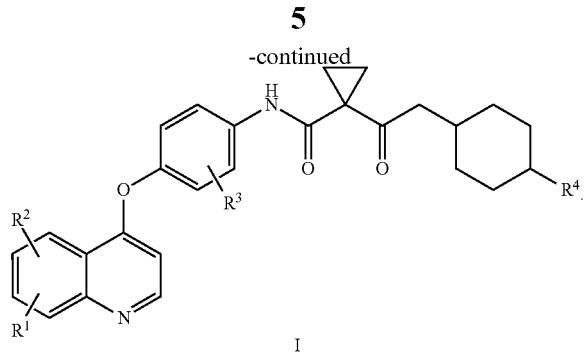

In some implementations, the base can include: potassium carbonate, sodium carbonate, sodium bicarbonate, triethyl amine (TEA), diisopropyl ethyl amine (DIPEA), pyridine, N,N-dimethylamino-4-pyridine (DMAP), and N-methylmorpholine (NMO), or combination thereof.

In another aspect, the present invention provides a method for generating a compound of Formula 9a, wherein $R^4$ is $^{18}F$, the method comprising:

i) reacting a compound of Formula 18 with a fluorinating reagent to generate a compound of Formula 22a:

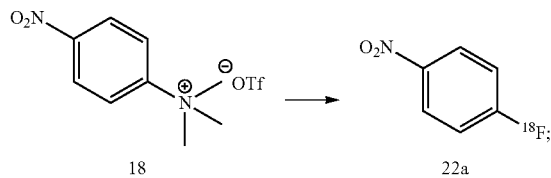

and ii) reducing the compound of Formula 22a to generate a compound of Formula 9a:

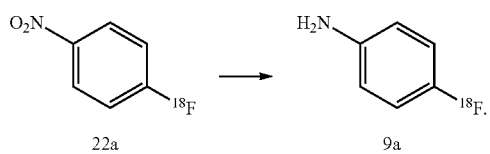

In some implementations, the fluorinating reagent is K[$^{18}$F] bound to a cryptand. In some embodiments, suitable cryptand compounds can include: 1,10-diaza-4,7,13,16,21, 24-hexaoxa-1,10-diazabicyclo[8.8.8]hexacosane (Kryptofix® 2.2.2. or Kryptofix 2.2.2 or Kryptofix 222). In some implementations, an exemplary fluorinating reagent is Kryptofix 2.2.2/K$^{18}$[F].

DETAILED DESCRIPTION OF THE INVENTION

Figure 1:
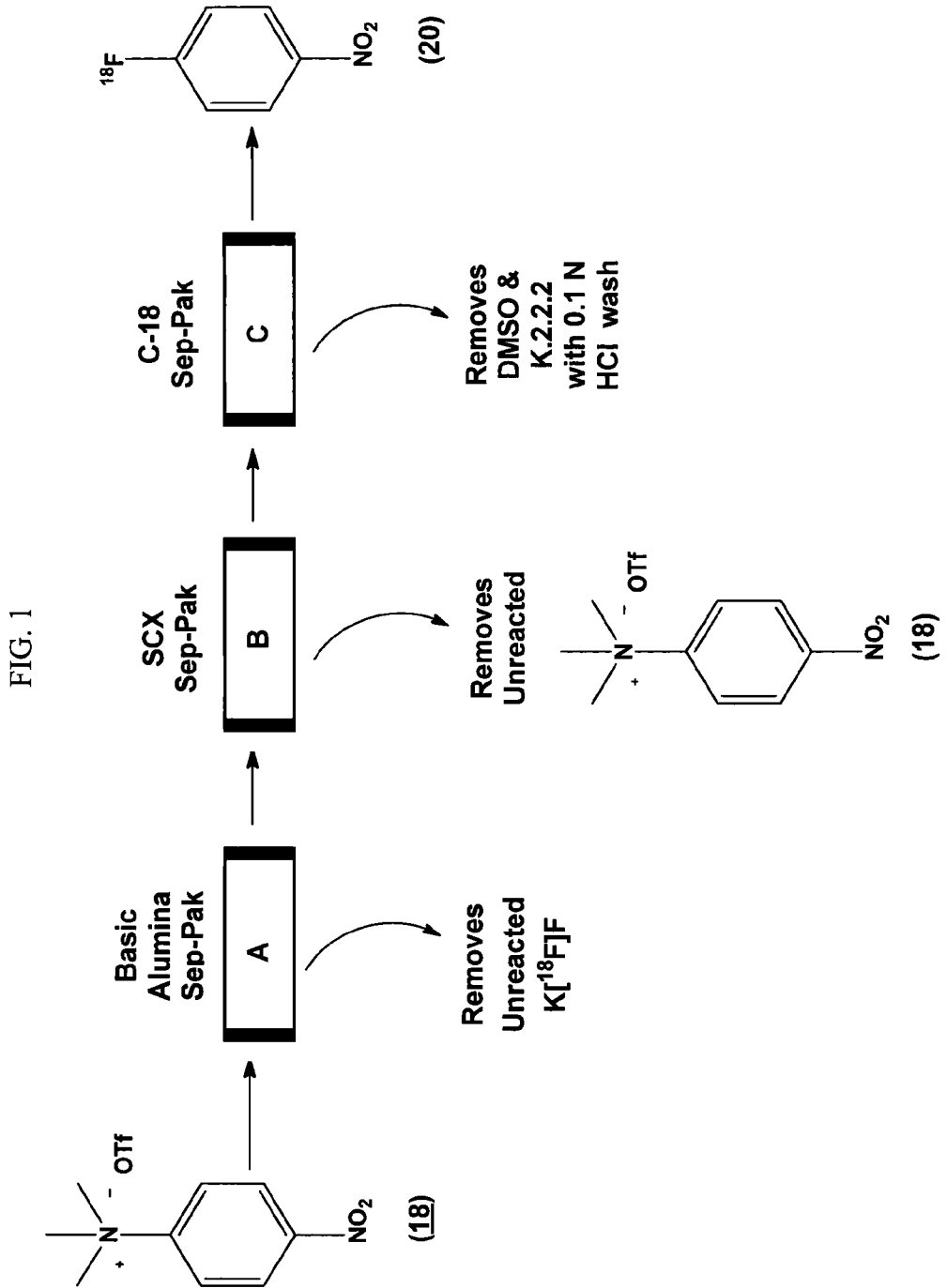
FIG. 1 depicts the solid phase extraction (SPE) purification of 1,4-[$^{18}$F]-fluoronitrobenzene.

As used herein, the following definitions shall apply unless otherwise indicated.

As used in the present specification, the following words and phrases are generally intended to have the meanings as set forth below, except to the extent that the context in which they are used indicates otherwise or they are expressly defined to mean something different.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

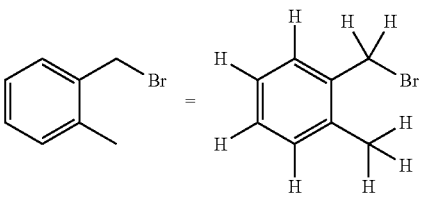

If a group "R" is depicted as "floating" on a ring system, as for example in the formula:

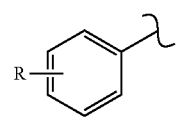

then, unless otherwise defined, a substituent "R" may reside on any atom of the ring system, assuming replacement of a depicted, implied, or expressly defined hydrogen from one of the ring atoms, so long as a stable structure is formed.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Alkyl" is intended to include linear, branched, or cyclic hydrocarbon structures and combinations thereof, inclusively. For example, "C$_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more than eight carbon atoms. Exemplary alkyl groups are those of C$_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl.

As used herein, a "halogen" or "halo" group refers to fluorine, chlorine, bromine or iodine.

"Haloalkoxy" refers to an alkoxy group which is substituted with one or more halogen atoms.

Cryptands are a family of synthetic and polycyclic multidentate ligands for a variety of cations. An exemplary cryptand can include: 1,10-diaza-4,7,13,16,21,24-hexaoxabicyclo[8.8.8]hexacosane, which is a [2.2.2]cryptand. Cryptands are commercially available under the tradename Kryptofix®. Cryptands with nitrogen atom(s) exhibit high affinity for alkali metal cations.

Adsorbents are materials that adsorb various chemicals and/or gases. Examples of adsorbents include silica gel (chemically inert, nontoxic, polar and stable up to 399° C.) zeolites, basic alumina, neutral alumina, octadecyl carbon chain (C18)-bonded silica column, C8-bonded silica, cyano-bonded silica and phenyl-bonded silica.

Ion exchange resins are ion exchangers that exchange ions from a solution and a complex. They are either cation exchangers that exchange positively charged ions (cations) or anion exchangers that exchange negatively charged ions (anions). There are also amphoteric exchangers that are able to exchange both cations and anions simultaneously.

"Pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference in their entirety.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, malic acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2 hydroxyethanesulfonic acid, benzenesulfonic acid, 4-chlorobenzenesulfonic acid, 2 naphthalenesulfonic acid, 4 toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" $8^{th}$ Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

Chemical structures and nomenclature disclosed and described herein are derived from ChemDraw, version 11.0.1, CambridgeSoft (Perkin Elmer) Cambridge, Mass.

Commonly Used Abbreviations and their Definitions

The following abbreviations and terms have the indicated meanings throughout.

| Abbreviation | Definition |
| --- | --- |
| BOP | Benzotriazole-1-yl-oxytripyrrolidinophosphonium hexafluorophosphate |
| br | broad |

| Abbreviation | Definition |
|---|---|
| Calcd | calculated |
| Ci | curie |
| COMU | (1-Cyano-2-ethoxy-2-oxoethylidenaminooxy)dimethylamino-morpholino-carbenium hexafluorophosphate |
| °C. | degrees Celsius |
| d | doublet |
| dd | doublet of doublets |
| di | de-ionized |
| dt | doublet of triplets |
| DBU | Diazabicylo[5.4.0]undec-7-ene |
| DCM | Dichloromethane (or) methylene chloride (or) $CH_2Cl_2$ |
| DCC | N,N-Dicyclohexylcarbodiimide |
| DIC | Diisopropylcarbodiimide |
| DIEA | N,N-Diisopropylethyl amine |
| DMAP | N-N-Dimethylamino-4-pyridine |
| DMF | Dimethylformamide |
| DMSO | Dimethyl sulfoxide |
| EDCI | 1-Ethyl-3-(3-dimethylaminopropyl)carbodiimide |
| EtOAc | Ethyl acetate |
| g | gram(s) |
| GBM | Glioblastoma multiforme |
| GBq | gigabecquerel |
| h or hr | hour(s) |
| HATU | 1-[Bis(dimethylamino)methylene]1H-1,2,3-triazolo[4,5-b]pyridinium-3-oxid hexafluorophosphate |
| HBTU | N,N,N',N'-Tetramethyl-O-(1H-benzotriazol-1-yl)uranium hexafluorophosphate |
| HGF | Hepatocyte growth factor |
| HOAt | 1-Hydroxy-7-azabenzotriazole |
| HOBt | Hydroxybenzotriazole |
| HPLC | high pressure liquid chromatography |
| Kryptofix 2.2.2 | 1,10-Diaza-4,7,13,16,21,24-hexaoxa-1,10-diazabicyclo[8.8.8]hexacosane |
| LCMS | liquid chromatography/mass spectral analysis |
| M | Molar or molarity |
| m | Multiplet |
| mCi | millicurie |
| Me | methyl |
| mg | milligram(s) |
| MHz | megahertz (frequency) |
| min | minute(s) |
| mL | milliliter(s) |
| mmoL | millimole(s) |
| MRI | Magnetic resonance imaging |
| MS | mass spectral analysis |
| MTC | medullary thyroid cancer |
| NaOH | Sodium hydroxide |
| NMO | N-methylmorpholine |
| NMR | Nuclear magnetic resonance spectroscopy |
| PET | Positron emission tomography |
| Ph | Phenyl |
| PyBOP | Benzotriazol-1-yl-oxytripyrrolidinophosphonium hexafluorophosphate |
| q | quartet |
| RT | room temperature |
| Rt | retention time |
| s | singlet |
| SPE | solid-phase extraction |
| t | triplet |
| TEA | Triethyl amine |
| TLC | thin layer chromatography |
| TOTU | O-[Ethoxycarbonyl]cyanomethyleneamino]-N,N,N',N'-tetramethyluronium tetrafluoroborate |
| THF | Tetrahydrofuran |
| UV | ultra-violet |
| μL | microliter(s) |
| μM | Micromolar |
| VEGF | vascular endothelial growth factor |
| VEGFR-2 | vascular endothelial growth factor receptor-2 |

Methods of Synthesis

In one aspect, the present invention provides a method for generating a compound of Formula I:

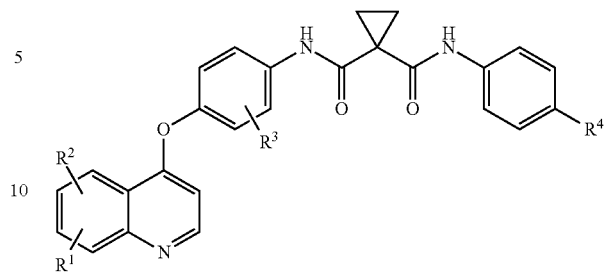

or a pharmaceutically acceptable salt thereof, wherein each of $R^1$ and $R^2$ is independently alkoxy or haloalkoxy; $R^3$ is H, F, Cl, I or Br; and $R^4$ is F, $^{18}F$, Cl, I or Br; the method comprising:

i) reacting a compound of Formula 8 with a compound of Formula 9 in the presence of a coupling reagent

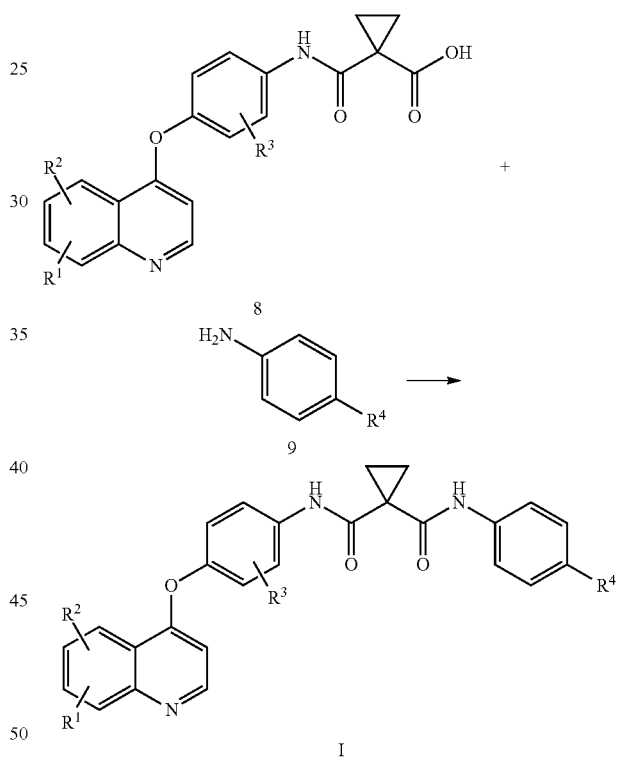

to generate a compound of Formula I.

In some implementations, the coupling reagent can include: N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent), benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), and (1-cyano-2-ethoxy-2-oxoethylidenaminooxy)dimethylamino-morpholino-carbenium hexafluorophosphate (COMU) or a combination thereof.

In some embodiments, the coupling reaction comprising a compound of Formula 8 and a compound of Formula 9 occurs in the presence of a tertiary amine base. In some examples, the tertiary amine base can include: diisopropylethyl amine (DIPEA), triethyl amine (TEA), N-methyl imidazole, pyridine, 4-(dimethylamino)pyridine (DMAP), 3,4-lutidine, 4-methoxypyridine, N-methylmorpholine (NMO), 1,4-diazabicycle[2.2.2]octane (DABCO), and 1,8-diazacycloundec-7-ene (DBU), or a combination thereof.

In some implementations, the coupling reaction comprising a compound of Formula 8 and a compound of Formula 9 occurs in the presence of an aprotic solvent. In some examples, the aprotic solvent can include: acetonitrile, diethyl ether, diisopropyl ether, 2-methoxyethyl ether, 1,2-dimethoxyethane, tert-butyl methyl ether, tetrahydrofuran, 1,4-dioxane, benzene, toluene, α,α,α-trifluorotoluene, cyclohexane, methylcyclohexane carbon tetrachloride, methylene chloride, N,N-dimethylformamide, dimethyl sulfoxide, and N-methyl-2-pyrrolidone or a combination thereof.

In some implementations, the coupling reaction comprising a compound of Formula 8 and a compound of Formula 9 is performed at temperatures ranging from about 20° C. to about 100° C., for example, from about 25° C. to about 100° C. In some embodiments, the coupling reaction is performed at ambient temperature, i.e. from about 20° C. to about 25° C. In some embodiments, the coupling reaction comprising a compound of Formula 8 and a compound of Formula 9 is performed at an elevated temperature ranging from about 80° C. to about 90° C. In other embodiments, the coupling reaction comprising a compound of Formula 8 and a compound of Formula 9 is performed at a temperature of about 85° C. The times necessary for the exemplified coupling reactions comprising a compound of Formula 8 and a compound of Formula 9, may vary with the identities of the reactants, the solvent system and the chosen temperature.

In another embodiment, the present invention provides a method for synthesizing a compound of Formula I:

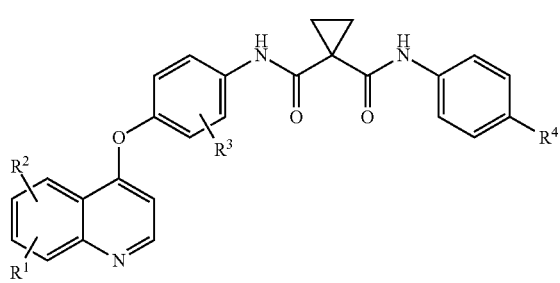

I or a pharmaceutically acceptable salt thereof, wherein each of $R^1$ and $R^2$ is independently alkoxy or haloalkoxy; $R^3$ is H, F, Cl, I or Br; and $R^4$ is F, $^{18}$F, Cl, I or Br; the method comprising:

i) reacting a compound of Formula 8 with a compound of Formula 9 in the presence of a coupling reagent and applying microwave radiation to the reaction to generate compound of Formula I:

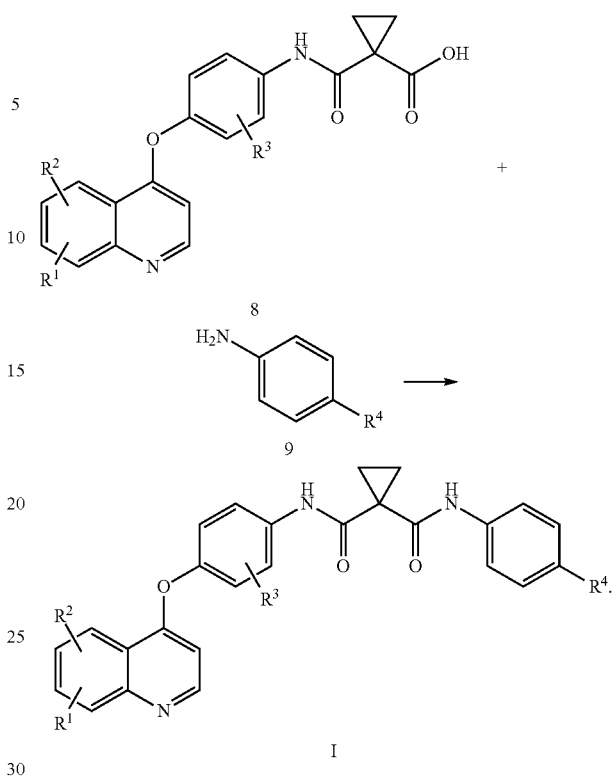

In some embodiments, when the coupling reaction is heated with microwave radiation, the coupling reaction times are shorter than when performing the coupling reaction in the absence of microwave heating. In some embodiments, the coupling reaction is performed with applied microwave radiation at power levels ranging from about 10 watts to about 50 watts. In other embodiments, the coupling reaction is performed using microwave radiation heating wherein the amount of microwave radiation ranges between about 10 watts to about 20 watts. The times necessary for the exemplified coupling reactions comprising a compound of Formula 8 and a compound of Formula 9, may vary with the identities of the reactants, the solvent system and the chosen temperature.

In some implementations, the coupling reagent can include: N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent), benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), and (1-cyano-2-ethoxy-2-oxoethylidenaminooxy)dimethylamino-morpholino-carbenium hexafluorophosphate (COMU, or a combination thereof.

In some implementations, the coupling reaction of a compound of Formula 8 and a compound of Formula 9 in the presence of microwave heating further comprises the addition of a tertiary amine base. In some examples, the tertiary amine base can include: diisopropylethyl amine (DIPEA), triethyl amine (TEA), N-methyl imidazole, pyridine, 4-(dimethylamino)pyridine (DMAP), 3,4-lutidine, 4-methoxypyridine, N-methylmorpholine (NMO), 1,4-diazabicycle[2.2.2]octane (DABCO), and 1,8-diazacycloundec-7-ene (DBU), or a combination thereof.

In some implementations, the coupling reaction of a compound of Formula 8 and a compound of Formula 9 in the presence of microwave heating further comprises the addition of an aprotic solvent. In some examples, the aprotic solvent can include: acetonitrile, diethyl ether, diisopropyl ether, 2-methoxyethyl ether, 1,2-dimethoxyethane, tert-butyl methyl ether, tetrahydrofuran, 1,4-dioxane, benzene, toluene, α,α,α-trifluorotoluene, cyclohexane, methylcyclohexane carbon tetrachloride, methylene chloride, N,N-dimethylformamide, dimethyl sulfoxide, and N-methyl-2-pyrrolidone, or a combination thereof.

In some implementations, the coupling reaction of a compound of Formula 8 and a compound of Formula 9, is heated to a temperature ranging from about 25° C. to about 100° C., or from about 80° C. to about 90° C., or about 85° C. using microwave radiation. The times necessary for the exemplified coupling reactions comprising a compound of Formula 8 and a compound of Formula 9, may vary with the identities of the reactants, the solvent system and the chosen temperature.

Another aspect of the present invention is directed to a method for generating a compound of Formula I:

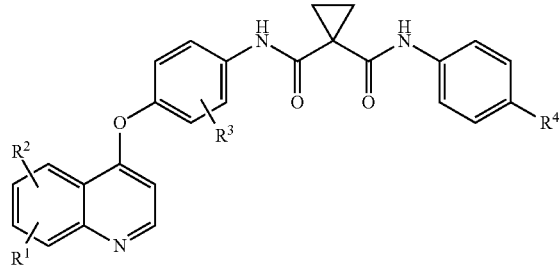

I or a pharmaceutically acceptable salt thereof wherein each of $R^1$ and $R^2$ is independently alkoxy or haloalkoxy; $R^3$ is H, F, Cl, I or Br; and $R^4$ is F, $^{18}$F, Cl, I or Br; comprising:

i) reacting a compound of Formula 8 with a chlorinating or brominating agent to generate acid halide 8a, wherein X is chloro or bromo:

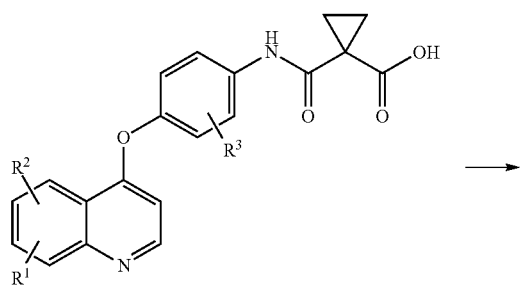

8

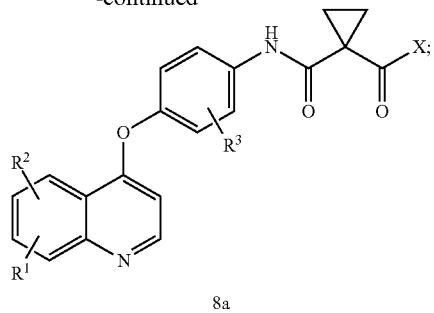

8a and ii) reacting the compound of Formula 8a with a compound of Formula 9 in the presence of a base to generate a compound of Formula (I) or a pharmaceutically acceptable salt thereof.

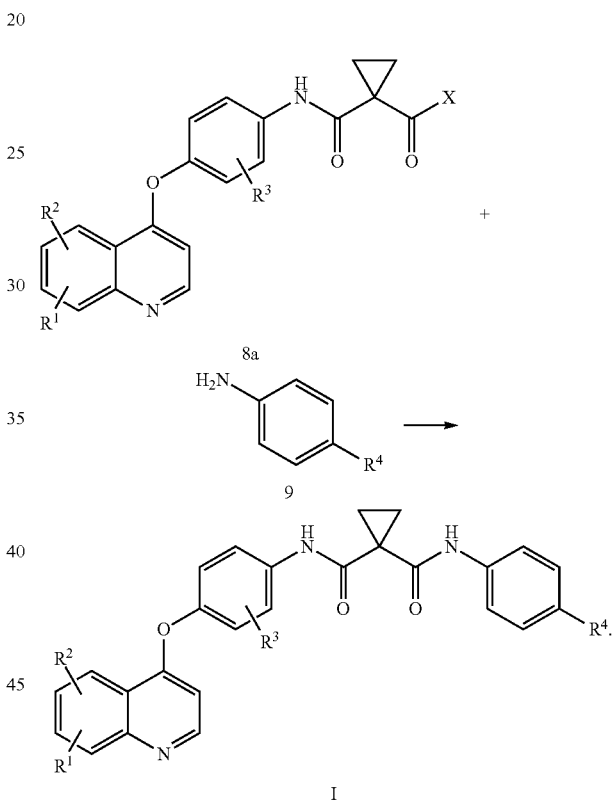

In some implementations, the chlorinating or brominating agent can include: thionyl chloride, thionyl bromide, oxalyl chloride, phosphorus pentachloride and phosphorus trichloride. In some embodiments, the chlorinating agent is oxalyl chloride.

In some implementations, the base can include: potassium carbonate, sodium carbonate, sodium bicarbonate, triethyl amine (TEA), diisopropylethyl amine (DIPEA), pyridine, 4-(dimethylamino)pyridine (DMAP), and N-methylmorpholine (NMO), or a combination thereof. In some embodiments, the base is potassium carbonate.

In some implementations, the above reactions can be performed at temperatures ranging from about 20° C. to about 40° C. In some embodiments, each reaction is performed at ambient temperature. The times necessary for the above exemplified reactions may vary with the identities of the reactants, the solvent system and the chosen temperature.

In one aspect, the present invention provides a method for generating the compound of Formula 9a, wherein $R^4$ is $^{18}F$, the method comprising:

i) reacting a compound of Formula 18 with a fluorinating reagent to generate a compound of Formula 22a:

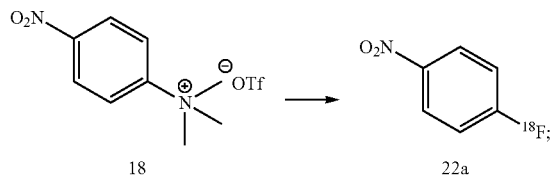

and ii) reducing the compound of Formula 22a to generate a compound of Formula 9a:

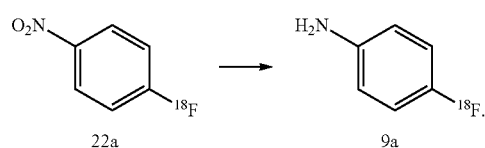

In some implementations, the fluorinating reagent is $K[^{18}F]$ bound to a cryptand. In some examples, a suitable cryptand is 1,10-diaza-4,7,13,16,21,24-hexaoxa-1,10-diazabicyclo[8.8.8]hexacosane (Kryptofix® 2.2.2. or Kryptofix 2.2.2 or Kryptofix 222). In some embodiments, the fluorinating reagent is Kryptofix 2.2.2/$K^{18}[F]$.

In some implementations, the fluorination reaction occurs in the presence of a polar aprotic solvent. In some embodiments, the polar aprotic solvent can include: N,N-dimethylformamide, dimethyl sulfoxide, acetonitrile, N-methyl-2-pyrrolidone, tetrahydrofuran, and 1,4-dioxane, or a combination thereof.

In some implementations, the compound of Formula 9a is purified by passing through a series of columns packed with adsorbents and/or ion exchange resins. In some embodiments, the adsorbents can include: silica gel, neutral alumina, basic alumina, octadecyl carbon chain (C18)-bonded silica column, C8-bonded silica, cyano-bonded silica, phenyl-bonded silica, or a combination thereof. In other exemplary embodiments, the ion exchange resin can include acidic or cation-exchange resins, for example, cation ion-exchange resins containing sulphonate anions.

In some embodiments, the crude reaction mixture containing the compound of Formula 9a, is further purified by passing the crude reaction mixture through three Sep-Pak cartridges connected in a series. In the first step, the crude reaction mixture is passed through a basic alumina Sep-Pak cartridge to remove unreacted fluorinating reagent (for example, $K[^{18}F]F$. In the second step, the resultant eluate is passed through a SCX Sep-Pak cartridge to remove unreacted trimethylanilinium salt (18). In the final step, the enriched eluate containing the compound of Formula 9a, is passed through a C-18 Sep-Pak cartridge to remove the reaction solvent (for example, dimethyl sulfoxide). The C-18 Sep-Pak cartridge is subsequently washed with 0.1N hydrochloric acid to remove any residual cryptand (for example, Kryptofix®). In some embodiments, the final purification of the compound of Formula 9a is accomplished by eluting the compound of Formula 9a though the C-18 Sep-Pak cartridge with methanol.

In some implementations, the reduction of the nitro group of the compound of Formula 22 is performed in the presence of a metal catalyst, an acid, and hydrogen. In some embodiments, the metal catalyst is derived from palladium, platinum, rhodium, or nickel. In other embodiments, the metal catalyst is palladium black. In some embodiments, the acid is mineral acid. More particularly, the mineral acid is phosphorus acid. In some embodiments, the reduction of the nitro group of the compound of Formula 22 is performed at temperatures ranging from about 25° C. to about 80° C. In some embodiments, the reduction of the nitro group of the compound of Formula 22 is performed at 60° C.

In another aspect, the present invention provides a method for generating a compound of Formula 1a, or a pharmaceutically acceptable salt thereof:

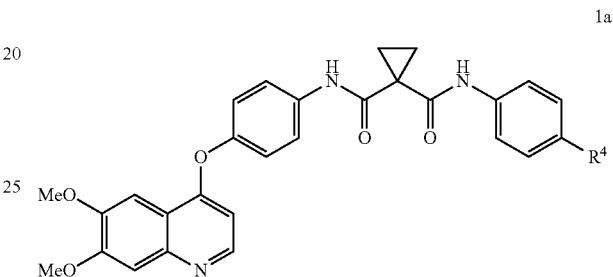

wherein, $R^4$ is F or $^{18}F$; the method comprising:

i) reacting a compound of Formula 10 with a chlorinating agent to generate a compound of Formula 11:

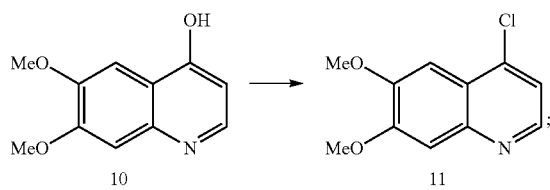 [SMILES: COc1cc2nccc(O)c2cc1OC ; COc1cc2nccc(Cl)c2cc1OC]

ii) coupling the compound of Formula 11 with a compound of Formula 23 in the presence of a base to generate a compound of Formula 12:

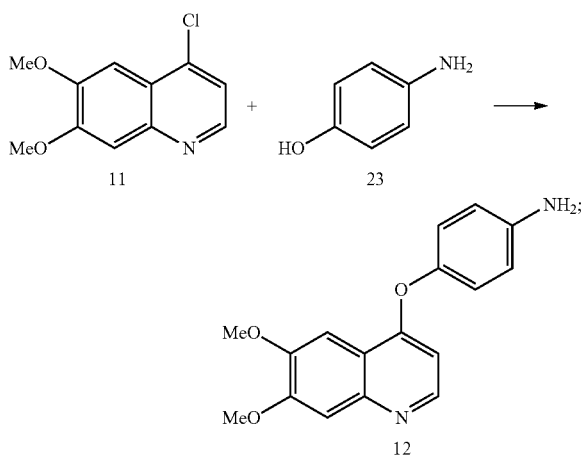

iii) coupling the compound of Formula 12 with a compound of Formula 13 in the presence of a coupling reagent to generate a compound of Formula 14:

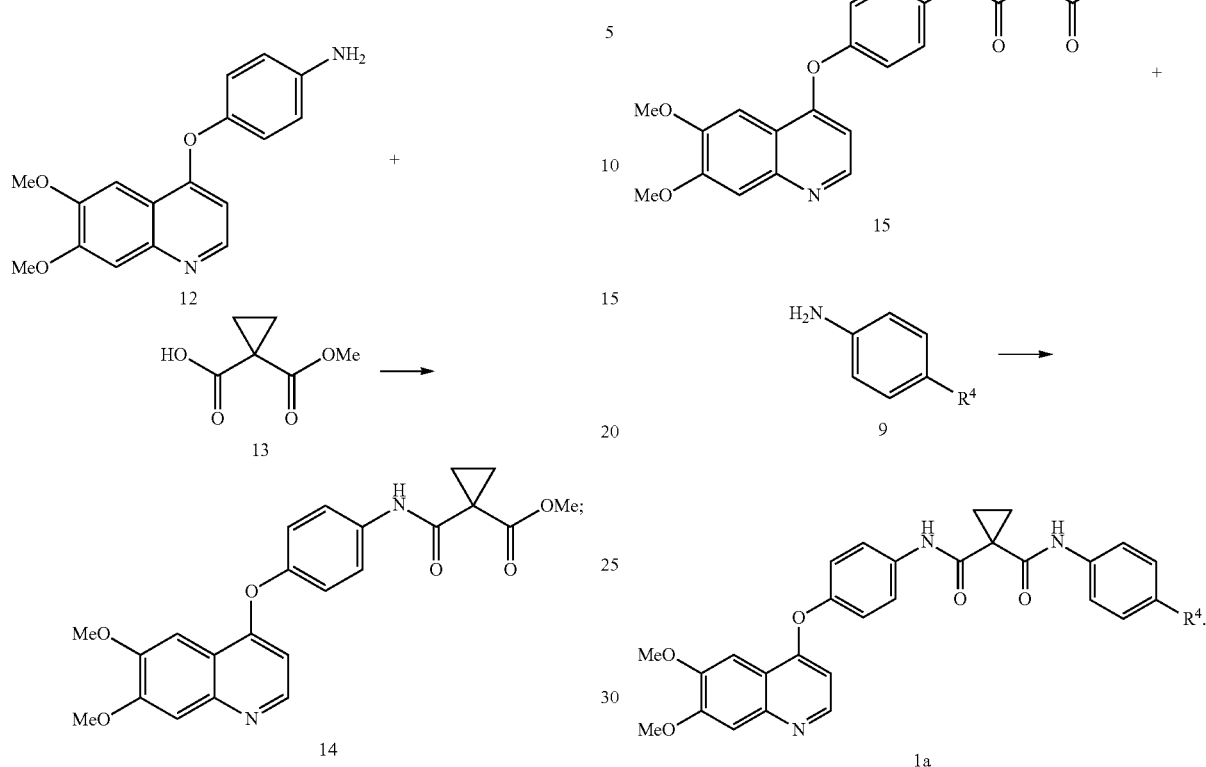

iv) saponifying the compound of Formula 14 in the presence of a base to generate a compound of Formula 15:

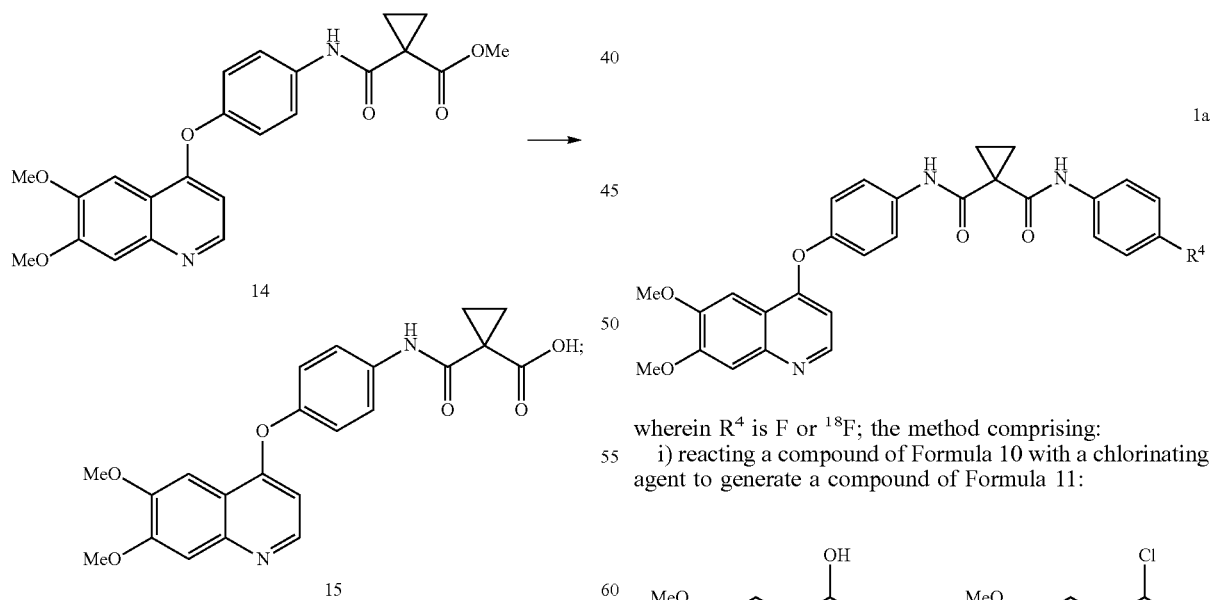

and v) coupling the compound of Formula 15 with a compound of Formula 9 in the presence of a coupling reagent to generate a compound of Formula 1a or a pharmaceutically acceptable salt thereof:

In another aspect, the present invention provides a method for generating a compound of Formula 1a, or a pharmaceutically acceptable salt thereof:

wherein $R^4$ is F or $^{18}F$; the method comprising:

i) reacting a compound of Formula 10 with a chlorinating agent to generate a compound of Formula 11:

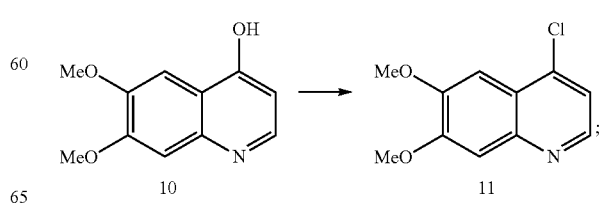

ii) coupling the compound of Formula 11 with a compound of Formula 23 in the presence of a base to generate a compound of Formula 12:

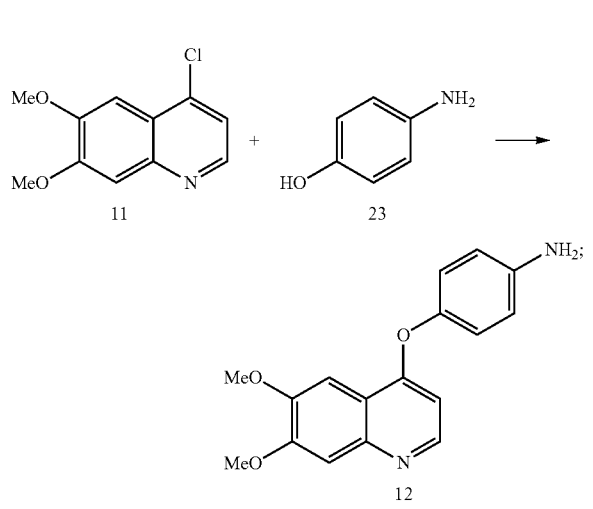

iii) coupling the compound of Formula 12 with a compound of Formula 13 in the presence of a coupling agent to generate a compound of Formula 14:

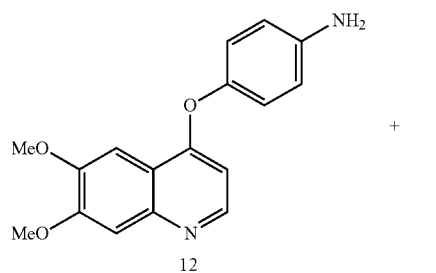

iv) saponifying a compound of Formula 14 in the presence of a base to generate a compound of Formula 15:

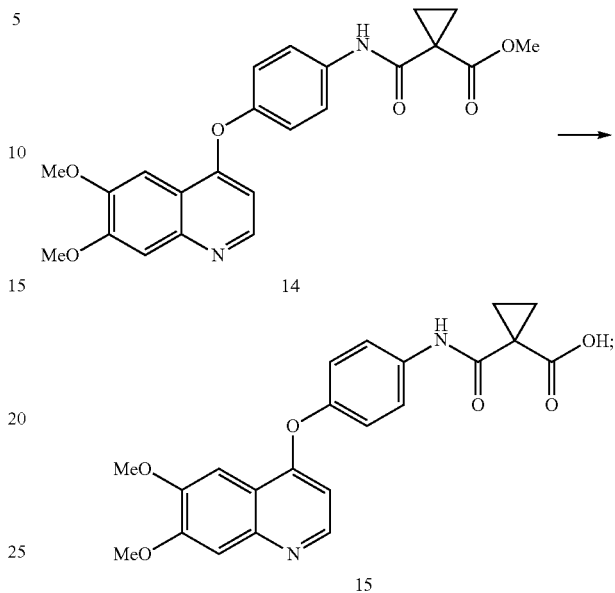

v) reacting the compound of Formula 15 with a halogenating reagent to generate a compound of Formula 15a;

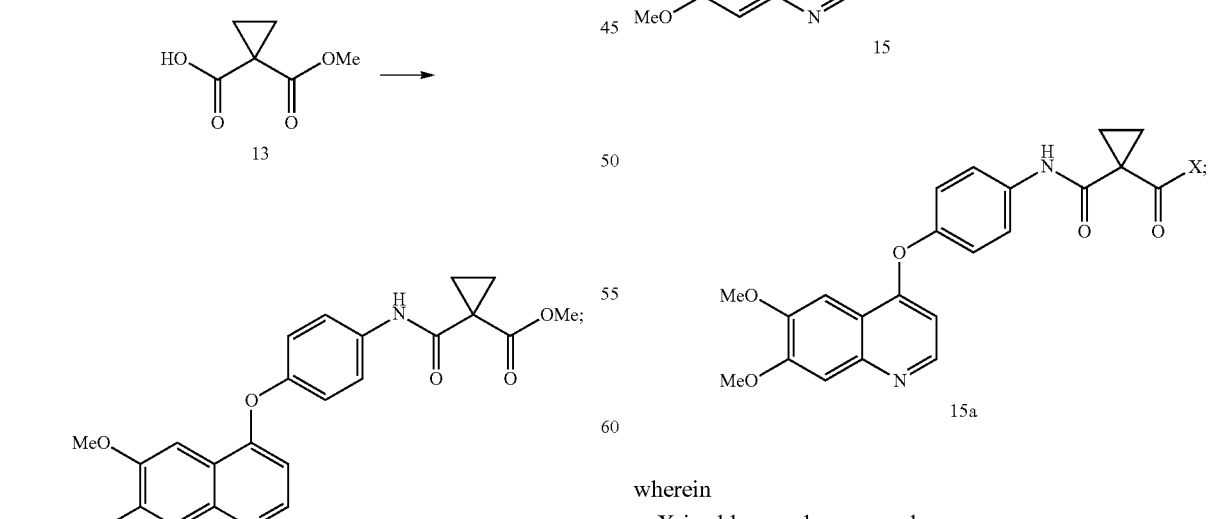

wherein
X is chloro or bromo; and
vi) reacting the compound of Formula 15a with a compound of Formula 9 to generate a compound of Formula 1a, or a pharmaceutically acceptable salt thereof:

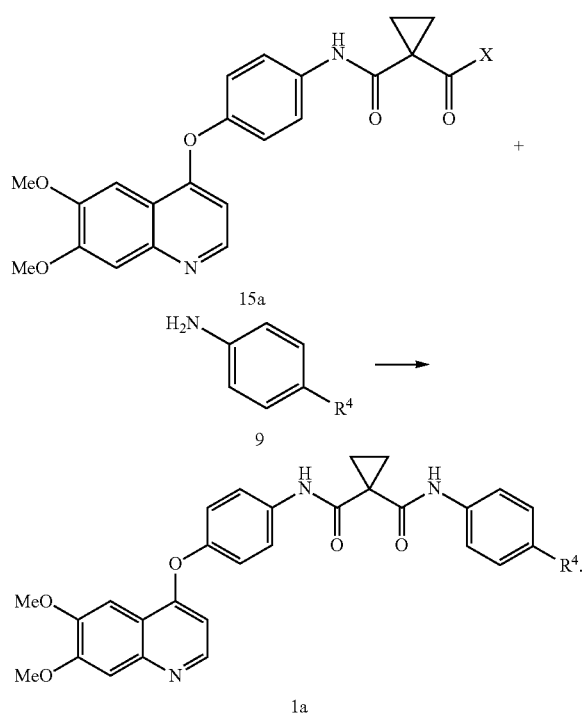

Illustrative Synthetic Schemes

Illustrative synthetic routes to prepare a compound of Formula I shown and described herein are exemplary only and are not intended, nor are they to be construed, to limit the scope of the present invention in any manner whatsoever. Those skilled in the art will be able to recognize modifications of the disclosed synthetic schemes and to devise alternate routes based on the disclosed examples provided herein; all such modifications and alternate routes are within the scope of the claims.

Scheme 1:

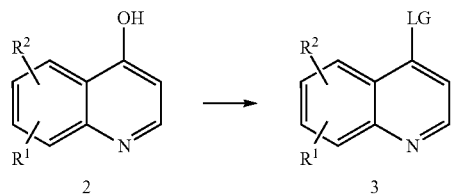

In illustrative Scheme 1, the compound of Formula 2 wherein $R^1$ and $R^2$ are as defined above can be converted to a compound of Formula 3, wherein LG represents a leaving group. Non-limiting examples of leaving groups that can be used include halo groups (e.g., Cl, Br, or F) that can be added by halogenating agents such as $SOCl_2$, $SO2Cl_2$, $COCl_2$, $PCl_5$, $POCl_3$, and the like. The reaction is advantageously carried out under suitable reaction conditions. Non-limiting examples of suitable reaction conditions in Scheme 1 can include the use of suitable solvents. Non-limiting example of suitable solvents that can be used during the halogenation of the compound of Formula 2 include a polar, aprotic solvent, such as $CH_3CN$, DMF, and the like, or mixtures thereof. In other embodiments, the chlorination can be carried out using $POCl_3$ in acetonitrile, $COCl_2$ in DMF, or $SOCl_2$ in DMF. The addition of the chlorination agent is advantageously carried out at a temperature ranging from about 60° C. to about 90° C. In another embodiment, the addition of the chlorination agent can be carried out at a temperature ranging from about 70° C. to about 85° C. In another embodiment, the addition of the chlorination agent can be carried out at a temperature ranging from about 74° C. to about 80° C. The product can then be collected by filtration and purified using standard techniques.

Scheme 2:

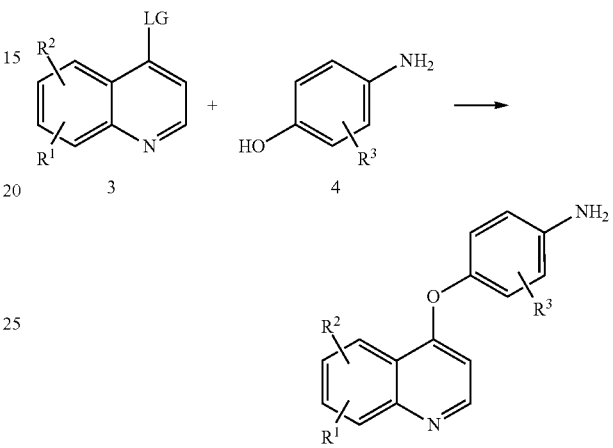

In illustrative Scheme 2, a compound of Formula 3 wherein $R^1$ and $R^2$ are as defined above, is reacted with a substituted 4-aminophenol 4 wherein $R^3$ is defined above, to generate a compound of Formula 5. A non-limiting example of a leaving group (LG) includes a halo group such as Cl, Br, or F. Various compounds of Formula 4 are commercially available, such as 2-fluoro-4-aminophenol and 4-aminophenol. Also, the skilled artisan would be able to make any variation of a compound of Formula 4 using commercially available starting materials and by using known techniques to modify these commercially available starting materials to yield various compounds within the scope of a compound of Formula 4.

The Scheme 2 reaction in this embodiment is advantageously carried out under suitable reaction conditions. Non-limiting examples of suitable reaction conditions include using suitable solvents such as polar solvents. Non-limiting examples of polar solvents that can be used include tetrahydrofuran (THF), dimethylacetamide (DMA), dimethylsulfoxide (DMSO), dimethylformamide (DMF), ethyl acetate, N-methyl pyrrolidone (NMP), propylene carbonate, and the like, or mixtures thereof. In another embodiment, the polar solvent is dimethylacetamide (DMA). In another embodiment, the polar solvent is dimethylsulfoxide (DMSO). In another embodiment, the polar solvent is dimethylformamide (DMF). In another embodiment, the polar solvent is ethyl acetate. In another embodiment, the polar solvent is N-methyl pyrrolidone (NMP). In another embodiment, the polar solvent is propylene carbonate. In another embodiment, the solvent is a mixture of solvents, such as a mixture comprising THF and DMA.

The reactant compounds of Formulas 3 and 4 can be added together at a temperature ranging from about 10° C. to about 30° C., or alternatively, from about 15° C. to about 28° C., or alternatively, from about 20° C. to about 25° C.

The mixture is then heated to a temperature ranging from about 80° C. to about 125° C., or alternatively, from about 95° C. to about 110° C., or alternatively, from about 100° C. to about 105° C., and the selected temperature is maintained until the reaction is complete.

Other non-limiting examples of suitable reaction conditions in Scheme 2 include the use of a suitable base, such as a metal hydroxide or a non-nucleophilic base. Examples of metal hydroxides include sodium hydroxide or potassium hydroxide. Non-limiting examples of non-nucleophilic bases that can be used include lithium diisopropylamide, lithium tetramethylpiperidide, and alkali metal alkoxides such as sodium tert-butoxide, potassium tert-butoxide, sodium-pentoxide, and the like, or mixtures thereof. Preferably, the base is sodium tert-butoxide or sodium tert-pentoxide. In one embodiment, the base is sodium tert-pentoxide. Typically the sodium tert-pentoxide is commercially available as 35 weight percent solution of base in tetrahydrofuran, or as a 95 weight percent solid reagent. Preferably, the sodium tert-pentoxide is a 95 weight percent solid.

Typically, approximately 1.1 to 3.0 molar equivalents of base are used relative the moles of compound of Formula 3 that are used. More preferably, 1.3 to 2.5 molar equivalents of base are used relative the moles of 3 that are used. More preferably, 1.5 to 2.2 molar equivalents of base are used relative to the moles of compound of Formula 3 that are used. More preferably, 1.7 to 2.1 molar equivalents of base are used relative to the moles of compound of Formula 3 that are used.

Typically, the amount of molar equivalents of amino phenol that are used exceeds the molar equivalents of base that are used. In one embodiment, 1.1 to 2 molar equivalents of amino phenol are used relative to the molar equivalents of base that are used.

Once the reaction is substantially complete, the reaction mixture can be cooled to a temperature ranging from about 10° C. to about 25° C. Precooled water can be charged at a rate to maintain a temperature that ranges from about 5° C. to about 35° C. Alternatively, the precooled water can be charged at a rate to maintain a temperature that ranges from about 10° C. to about 25° C. As a non-limiting example, the precooled water can be at a temperature ranging from about 0° C. to about 10° C. As another non-limiting example, the precooled water can be at a temperature ranging from about 2° C. to about 7° C. The precipitate can be collected by filtration under standard conditions and purified by standard purification techniques.

Scheme 3:

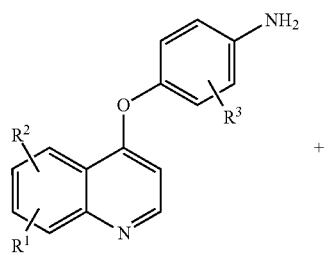

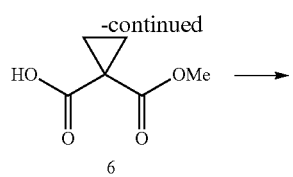

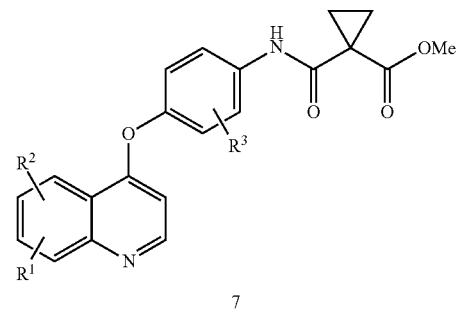

In illustrative Scheme 3, an amine compound of Formula 5 wherein $R^1$ and $R^2$ are as defined above, is coupled with 1-(methoxycarbonyl)cyclopropanecarboxylic acid 6 in the presence of a coupling reagent to generate an amide compound of Formula 7. Examples of suitable coupling reagents include: N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent) benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), (1-cyano-2-ethoxy-2-oxoethylidenaminooxy)dimethylamino-morpholino-carbenium hexafluorophosphate (COMU) or a combination thereof. Suitable reaction solvents include, but are not limited to aprotic solvents. Suitable examples of aprotic solvents useful in the reaction shown in Scheme 3, can include: acetonitrile, diethyl ether, diisopropyl ether, 2-methoxyethyl ether, 1,2-dimethoxyethane, tert-butyl methyl ether, tetrahydrofuran (THF), 1,4-dioxane, benzene, toluene, α,α,α-trifluorotolune, cyclohexane, methylcyclohexane carbon tetrachloride, methylene chloride (DCM), N,N-dimethylformamide (DMF), dimethyl sulfoxide (DMSO), N-methyl-2-pyrrolidone (NMP) or a combination thereof. The times necessary for the exemplified coupling reactions comprising a compound of Formula 5 and a compound of Formula 6, may vary with the identities of the reactants, the solvent system and the chosen temperature. Exemplary reaction times can range from about 2 hours to about 10 hours. In some embodiments, the reaction time is about 5 hours. The reaction can be performed at temperatures ranging from about 20° C. to about 30° C.

Scheme 4:

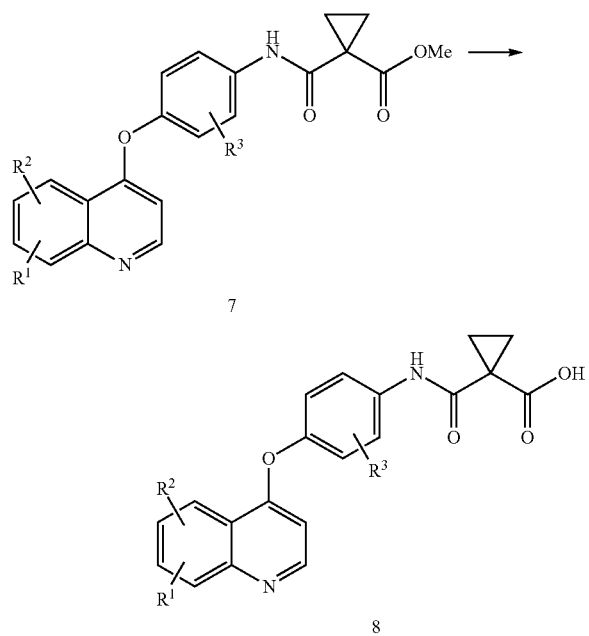

In illustrative Scheme 4, the ester compound of Formula 7 wherein $R^1$ and $R^2$ are as defined above, is saponified in the presence of an alkaline or an alkaline earth metal hydroxide to generate an acid compound of Formula 8. Examples of alkaline or alkaline metal hydroxides can include: sodium hydroxide, lithium hydroxide, caesium hydroxide, and potassium hydroxide. Suitable solvents can include methanol, ethanol, isopropanol, isopropanol, water or a combination thereof. The times necessary for the exemplified saponification reaction comprising a compound of Formula 7 may vary with the identities of the reactants, the solvent system and the chosen temperature. Exemplary reaction times can range from about 5 hours to about 32 hours. In some embodiments, the reaction time is about 24 hours. The reaction can be performed at temperatures ranging from about 20° C. to about 45° C.

Scheme 5:

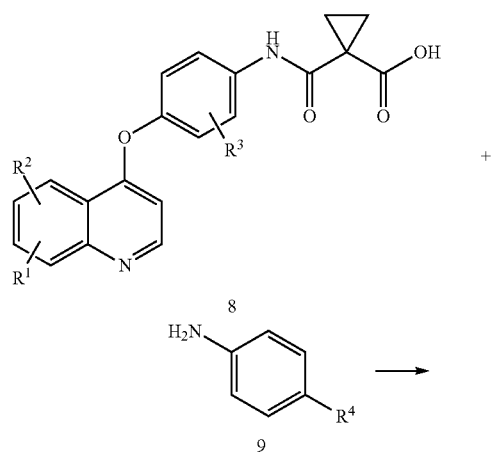

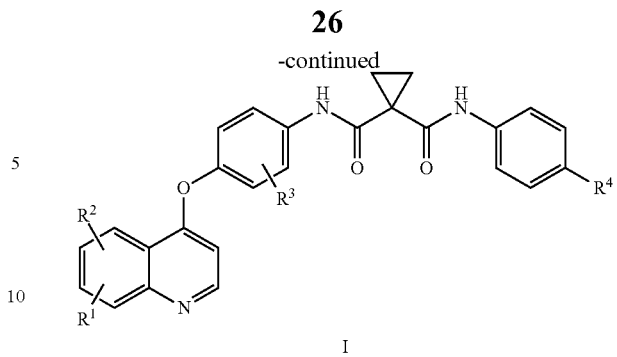

In illustrative Scheme 5, the coupling of the acid compound of Formula 8 wherein $R^1$ and $R^2$ are as defined above, with the aniline compound of Formula 9, wherein $R^4$ is F, $^{18}F$, I, Cl, or Br, can occur in the presence of a coupling reagent to generate the amide compound of Formula I. Examples of suitable coupling reagents include: N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent) benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), (1-cyano-2-ethoxy-2-oxoethylidenaminooxy)dimethylamino-morpholino-carbenium hexafluorophosphate (COMU) or a combination thereof.

Suitable solvents for the use in the coupling reaction of Scheme 5, can include, but are not limited to aprotic solvents. Examples of aprotic solvents include: acetonitrile, diethyl ether, diisopropyl ether, 2-methoxyethyl ether, 1,2-dimethoxyethane, tert-butyl methyl ether, tetrahydrofuran (THF), 1,4-dioxane, benzene, toluene, α,α,α-trifluorotoluene, cyclohexane, methylcyclohexane carbon tetrachloride, methylene chloride (DCM), N,N-dimethylformamide (DMF), dimethyl sulfoxide (DMSO), N-methyl-2-pyrrolidone (NMP) or a combination thereof.

The coupling reaction of Scheme 5 can be assisted by heating the reactants using microwave radiation ranging from about 10 watts to about 50 watts. In some embodiments, the coupling reaction of Scheme 5 can proceed in the presence of a base, for example: diisopropylethyl amine (DIPEA), triethyl amine (TEA), N-methyl imidazole, pyridine, N,N-dimethylamino-4-pyridine (DMAP), 3,4-lutidine, 4-methoxypyridine (NMO), 1,4-diazabicycle[2.2.2]octane (DABCO), 1,8-diazabicyloundec-7-ene (DBU) or a combination thereof.

The coupling reaction of Scheme 5 can be heated to a desired temperature varying from about 25° C. to about 100° C. In some embodiments, the coupling reaction of Scheme 5 can be heated to the desired temperature using microwave radiation. In some embodiments, the coupling reaction when heated to a temperature ranging from about 25° C. to about 100° C. using microwave radiation results in shorter reaction times compared to the coupling reaction without microwave heating. The reaction times necessary for the exemplified coupling reaction comprising a compound of Formula 8 and a compound of Formula 9 may vary with the identities of the reactants, the solvent system and the chosen temperature. In some embodiments, the reactants of the coupling reaction of Scheme 5 can be heated using about 10 watts to about 20 watts of microwave radiation to reach the desired temperature of from about 25° C. to about 100° C., which provides a higher yield of the desired product.

Scheme 6:

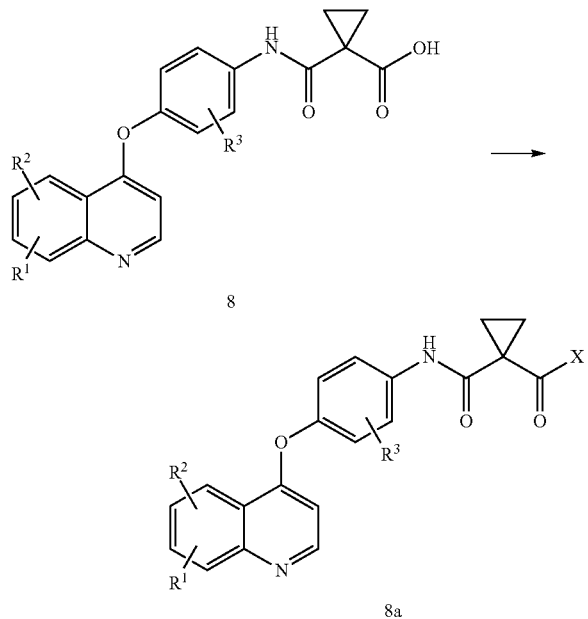

In illustrative Scheme 6, the acid compound of Formula 8, wherein R¹ and R² are as defined above, is reacted with a halogenating agent to generate the corresponding acid halide compound 8a, wherein X is chloro or bromo. Examples of suitable halogenating agents include: thionyl chloride, thionyl bromide, oxalyl chloride, phosphorus pentachloride or phosphorus trichloride. Suitable solvents for the reaction include diethyl ether, diisopropyl ether, 2-methoxyethyl ether, 1,2-dimethoxyethane, tert-butyl methyl ether, tetrahydrofuran (THF), 1,4-dioxane, benzene, toluene, α,α,α-trifluorotoluene, cyclohexane, methylcyclohexane or a combination thereof. The reaction times necessary for the exemplified halogenation reaction of Scheme 6 comprising a compound of Formula 8 may vary with the identities of the reactants, the solvent system and the chosen temperature. In some embodiments, the reaction of Scheme 6 may proceed at a desired temperature ranging from about 20° C. to about 25° C.

Scheme 7:

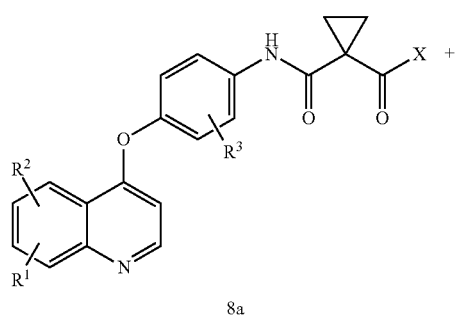

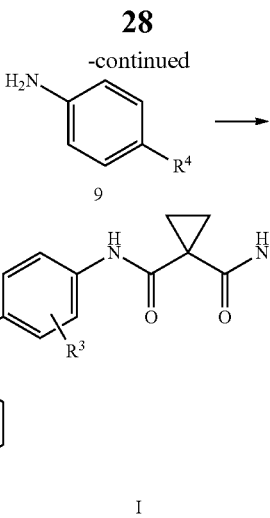

In illustrative Scheme 7, the compound of Formula 8a, wherein R¹ and R² are as defined above and X is chloro or bromo, is coupled with an aniline compound 9 in the presence of a base to yield a compound of Formula I. Suitable bases for use in the reaction of Scheme 7 can include potassium carbonate, sodium carbonate, sodium bicarbonate, triethyl amine (TEA), diisopropyl ethyl amine (DIPEA), pyridine, N,N-dimethylamino-4-pyridine (DMAP) or N-methylmorpholine (NMO). Suitable solvents include water, ethanol, isopropanol, dimethyl sulfoxide or a combination thereof. The reaction times necessary for the exemplified coupling reaction of Scheme 7 comprising a compound of Formula 8a and a compound of Formula 9 may vary with the identities of the reactants, the solvent system and the chosen temperature. In some embodiments, the reaction of Scheme 7 may proceed at a desired temperature ranging from about 20° C. to about 25° C.

EXAMPLES

Additional embodiments are disclosed in further detail in the following examples, which are not in any way intended to limit the scope of the claims.

Materials and General Methods

[$^{18}$F]-Fluoride was purchased from P.E.T. Net® Pharmaceuticals. Inc. All reagents were obtained from Aldrich Chemical Company or Lancaster® and were either ACS grade or of the highest quality material commercially available. Zorbax C18 analytical, semi-preparative HPLC columns, 25 mm (0.45 μm) nylon syringe filters (Pall P.N. 4438T), Merck LiChrolut® SCX (P.N. 48219-242), and Merck LiChrolut® EN cartridges (P.N. 48219-232 200 mg) were obtained from VWR Inc. Basic alumina light (Waters P.N. WAT023555, 280 mg), C18-plus (Waters P.N. WAT 020515, 360 mg), and QMA light (Waters P.N. WAT023525, 130 mg) were obtained from Waters. Microvials (5 ml) were obtained from Kontes. The microwave heating model RI 520A was obtained from Resonance Instruments Inc. (Skokie, Ill.). Mass spectra were obtained with a Finnigan TSQ or a Finnigan LCQ mass spectrometer. Proton NMR spectra were recorded on a Jeol EC+500 MHz NMR.

All reported radiochemical yields were decay corrected to the start of the radiochemical synthesis. HPLC purification and analysis was performed on a Varian Prostar HPLC system consisting of two pumps, a Varian UV detector and a Lab Logic γ-RAM radioactive flow through detector. Radiochemical purity was determined by analytical HPLC.

System A, in this system analytical samples were loaded into a Zorbax SB C18 column (4.6×250 mm) with a mobile phase of 50% MeCN and 50% 25 mM potassium phosphate dibasic solution (pH 9.0) at a flow rate of 1 ml/min. The UV detector was set at 254 nm. System B, In this system, analytical samples were loaded into a Luna C-8(2) column (4.6×150 mm) with a gradient program using a mobile phase that went from 5% MeCN and 95% 0.1% TFA at a flow rate of 1 ml/min at time 0 min to 95% MeCN and 5% 0.1% TFA at a flow rate of 1 ml/min at time 30 min. The UV detector was set at 254 nm. RadioTLC was completed on a Bioscan AR2000 using uniplate—Silica Gel GHLF, scored 10×20 cm, 250 microns TLC plates and an 8% methanol in dichloromethane as the solvent.

Example 1. Synthesis of 4-chloro-6,7-dimethoxy-ouinolone (11) from 6,7-Dimethoxy-quinolin-4-ol (10)

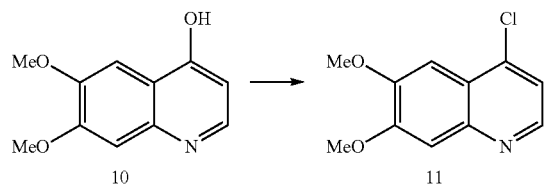 [SMILES: COc1cc2nccc(O)c2cc1OC ; COc1cc2nccc(Cl)c2cc1OC]

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl₃, 130.6 kg) was added. After the addition of POCl₃, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2-7° C. and then quenched into a chilled solution of dichloromethane (DCM, 482.8 kg), 26% NH₄OH (251.3 kg), and water (900 L). The resulting mixture was warmed to approximately 20-25° C., and phases were separated. The organic phase was filtered through a bed of AW hyflo super-cel NF (Celite; 5.4 kg) and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate which was then filtered and washed with n-heptane (92.0 kg), and dried on a filter at approximately 25° C. under nitrogen to afford the title compound. (35.6 kg).

Example 2. Synthesis of 4-(6,7-dimethoxyquinolin-3-yloxy)aniline (12)

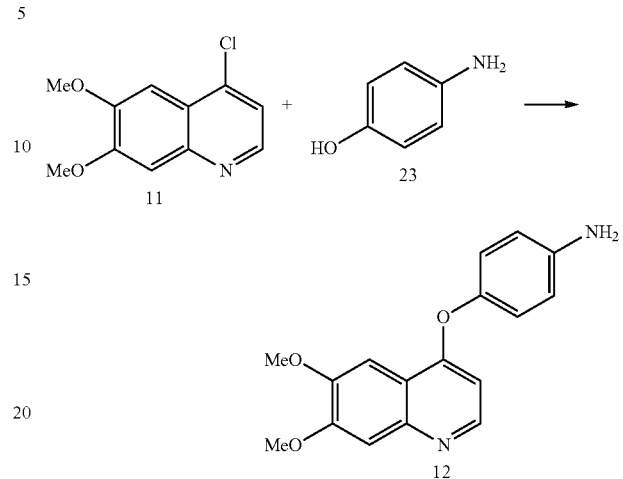

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg) and DMA (167.2 kg) at 20-25° C. This mixture was then heated to 100-105° C. for approximately 13 hours. After the reaction was deemed complete as determined using in-process HPLC analysis (<2% starting material remaining), the reactor contents were cooled at 15 to 20° C. and water (pre-cooled, 2 to 7° C., 587 L) charged at a rate to maintain 15 to 30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0-5° C. and aged for approximately 1 h after which time the solid was filtered, washed with THF (147.6 kg) and dried on a filter under vacuum at approximately 25° C. to yield 4-(6,7-dimethoxyquinolin-3-yloxy)aniline (34.0 kg).

Example 3. Synthesis of methyl 1-(4-(6,7-dimethoxyquinolin-3-yloxy)phenylcarbamoyl)cyclopropanecarboxylate (14)

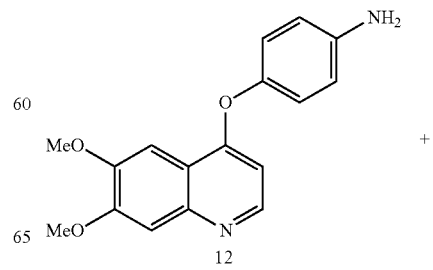

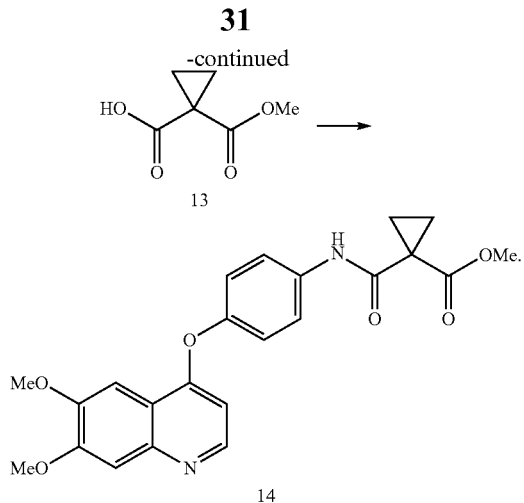

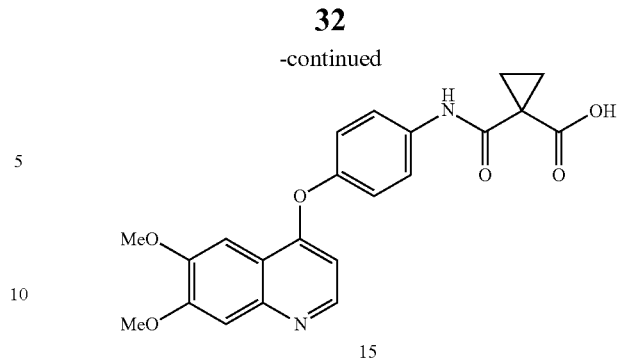

1-(Methoxycarbonyl)cyclopropanecarboxylic acid (13, 0.2 g, 1.2 mmol), 1,3-diisopropylcarbodiimide (0.2 mL, 1.2 mmol), and 1-hydroxybenzotriazole monohydrate (0.2 g, 1.2 mmol) were added to a 25 mL round bottom flask and dissolved in DMF (3.2 mL). This reaction mixture was allowed to stir at ambient temperature for 10 minutes. To it 4-(6,7-dimethoxyquinolin-3-yloxy)aniline (12, 0.3 g, 1.0 mmol) was added to reaction mixture, and allowed to stir at ambient temperature for 4.5 hours. After this time period, 100 mL of DI water was added and the reaction mixture was extracted with 3×50 mL of ethyl acetate. The organic layer was dried over sodium sulfate and concentrated to afford a yellow/white solid. The crude reaction mixture was purified via flash silica gel column chromatography using ethyl acetate as the mobile phase. Methyl 1-(4-(6,7-dimethoxyquinolin-3-yloxy)phenylcarbamoyl)cyclopropanecarboxylate (14, 0.4 g, 0.9 mmol, 89% yield) was obtained as white solid. $^1$H NMR (CDCl$_3$, 500 MHZ) δ 10.95 (s, 1H); 8.45 (d, 1H, J=5.5 Hz); 7.67 (d, 2H, J=6.6 Hz); 7.54 (s, 1H); 7.41 (s, 1H); 7.15 (d, 2H, J=6.6 Hz); 6.43 (d, 1H, J=5.5 Hz); 4.04 (s, 6H); 3.75 (s, 3H); 1.85-1.82 (m, 2H), 1.71-1.69 (m, 2H); LCMS (m/z) C$_{23}$H$_{23}$N$_2$O$_6$ (M+H) Calcd: 423.16. Found: 423.1; $^{13}$C NMR (CDCl$_3$, 125 mHz) δ 174.4, 166.9, 160.9, 152.9, 150.4, 149.5, 148.8, 146.8, 135.6, 121.9, 121.6, 116.1, 107.8, 103.3, 99.5, 56.1, 52.5, 26.5, 20.9.

Example 4. Synthesis of 1-(4-(6,7-dimethoxyquinolin-3-yloxy)phenylcarbamoyl)cyclopropanecarboxylic acid (15)

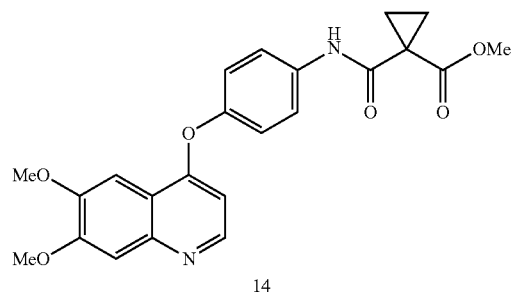

Methyl 1-(4-(6,7-dimethoxyquinolin-3-yloxy)phenylcarbamoyl)cyclopropanecarboxylate (14, 0.3 mg, 0.6 mmol) was dissolved in methanol (5.0 mL) and heated at 35-45° C., sodium hydroxide (1.0N, 1.0 mL, 1.0 mmol) was then added to the reaction mixture and was allowed to stir at 35-45° C. over a 24 hour period. The reaction was then concentrated to afford the 1-(4-(6,7-dimethoxyquinolin-3-yloxy)phenylcarbamoyl)cyclopropanecarboxylic acid (15, 0.2 g, 0.5 mmol, 88% yield) as a light yellow solid. The crude product was taken up in DI water (5.0 mL) and the pH of the solution was adjusted to 3 with concentrated sulfuric acid (0.5 ml, 1.0 mmol), yielding a white precipitate. The white precipitate was filtered, washed with 3 portions of DI water (5.0 mL) and then lyophilized over a 24 hour period and finally dried in a vacuum oven at 70° C. for 24 hours to afford 1-(4-(6,7-dimethoxyquinolin-3-yloxy)phenylcarbamoyl)cyclopropanecarboxylic acid (15, 0.2 mg, 0.5 mmol, 88% yield). HRMS (m/z) C$_{22}$H$_{21}$N$_2$O$_6$ (M+H) Calcd 409.13992. found 409.14007; $^1$H NMR (d$_6$-DMSO, 500 MHZ) δ 8.64 (d, 1H, J=6.6 Hz); 7.83 (s, 1H); 7.81 (d, 2H, J=8.8 Hz); 7.44 (s, 1H); 7.33 (d, 2H, J=8.8 Hz); 6.91 (d, 1H, J=6.6 Hz); 4.13 (s, 3H); 4.08 (s, 3H); 1.83-1.68 (m, 4H); $^{13}$C NMR (d$_6$-DMSO, 125 mHz) δ 168.3, 163.7, 158.5, 154.3, 153.5, 150.1, 143.4, 138.8, 135.9, 123.6, 122.7, 117.5, 108.2, 101.6, 100.2, 57.4, 57.1, 20.9, 20.2.

Example 5. Preparation of 1-[4-(6,7-dimethoxyquinolin-4-yloxy)-phenylcarbamoyl]-cyclopropanecarboxylic acid (15)

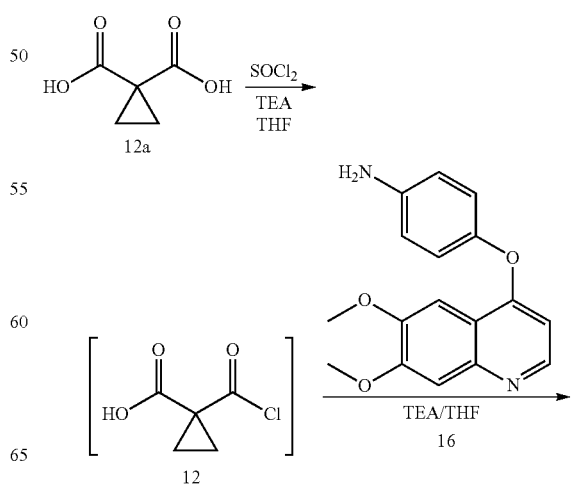

33

-continued

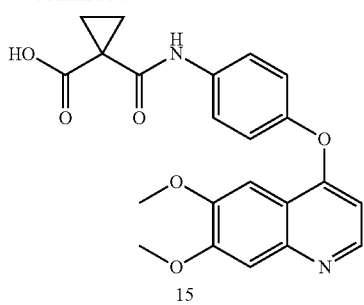
15

34

-continued

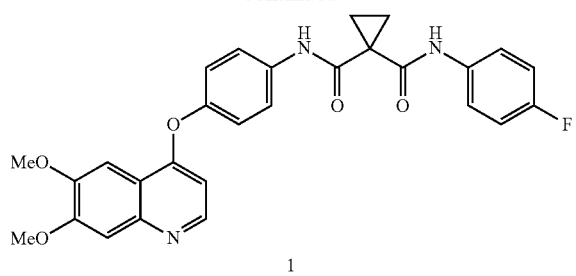
1

Preparation of 1-[4-(6,7-dimethoxy-quinolin-4-yloxy)-phenylcarbamoyl]-cyclopropanecarboxylic acid 15. To the cyclopropyl di-carboxylic acid 12a (449 mg, 3.45 mmol) in THF (3.5 mL) was added TEA (485 µL, 3.45 mmol). The resulting solution was stirred at room temperature under a nitrogen atmosphere for 40 minutes before adding thionyl chloride (250 µL, 3.44 mmol). The reaction was monitored by LCMS for the formation of mono acid chloride 12 (quenched the sample with MeOH and looked for corresponding mono methyl ester). After 3 hours stirring at room temperature, 4-(6,7-dimethoxy-quinolin-4-yloxy)-phenylamine 16 (1.02 g, 3.44 mmol) was added as a solid, followed by more THF (1.5 mL). Continued to stir at room temperature for 16 hours. The resulting thick slurry was diluted with EtOAc (10 mL) and extracted with 1N NaOH. The biphasic slurry was filtered and the aqueous phase was acidified with conc. HCl to pH=6 and filtered. Both solids were combined and washed with EtOAc, then dried under vacuum. The desired product, 1-[4-(6,7-dimethoxy-quinolin-4-yloxy)-phenylcarbamoyl]-cyclopropanecarboxylic acid, 15 was obtained (962 mg, 68.7% yield, 97% pure) as a white solid. $^1$H NMR (D$_2$O/NaOH): 7.97 (d, 1H), 7.18 (d, 2H), 6.76 (m, 4H), 6.08 (d, 1H), 3.73 (s, 3H), 3.56 (s, 3H), 1.15 (d, 4H).

Example 6. Synthesis of Cabozantinib (1)

Method A: Cabozantinib (1) was obtained via a microwave-assisted reaction with 4-fluoroaniline, HATU, DIPEA, and 1-(4-(6,7-dimethoxyquinolin-4-yloxy)phenylcarbamoyl)cyclopropanecarboxylic acid (15) in 80% isolated yields. Using a capped microvial in the microwave apparatus, microwave powers of greater than 50 W led to vigorous refluxing of these solutions; therefore, powers of 10-50 W were investigated. It was determined that using lower wattages of 10-20 W, allowed the reaction temperature to reach 85° C. over a 20 minute period.

Method B: To a solution of 1-(4-(6,7-dimethoxyquinolin-4-yloxy)phenylcarbamoyl)cyclopropanecarboxylic acid (15, 123 mg, 0.30 mmol), 4-fluoroaniline (40 mg, 0.36 mmol), DIPEA (234 mg, 1.81 mmol) and DMF (3 mL) was added (benzotriazol-1-yloxy)tripyrrolidinophosphonium hexafluorophosphate (PyBOP, 470 mg, 0.90 mmol) with stirring at 25° C. The resulting solution was stirred at 25° C. for 1 h. The mixture was diluted with EtOAc, washed with 0.2 N NaOH, and brine, dried with MgSO$_4$. Removal of EtOAc and column chromatography gave the desired product 1 (133 mg, 88% yield). $^1$H NMR (DMSO-d$_6$): 10.20 (s, 1H), 10.07 (s, 1H), 8.47 (d, 1H), 7.77 (d, 2H), 7.65 (m, 2H), 7.50 (s, 1H), 7.39 (s, 1H), 7.24 (dd, 2H), 7.16 (m, 2), 6.42 (d, 1H), 3.94 (s, 3H), 3.93 (s, 3H), 1.47 (s, 4H) ppm. LC/MS: Calcd for [M+H]$^+$ 502.2. found 502.2. Anal. HPLC (10 min gradient): 97.5% purity, 6.62 min.

Example 7. Synthesis of Cabozantinib (1)

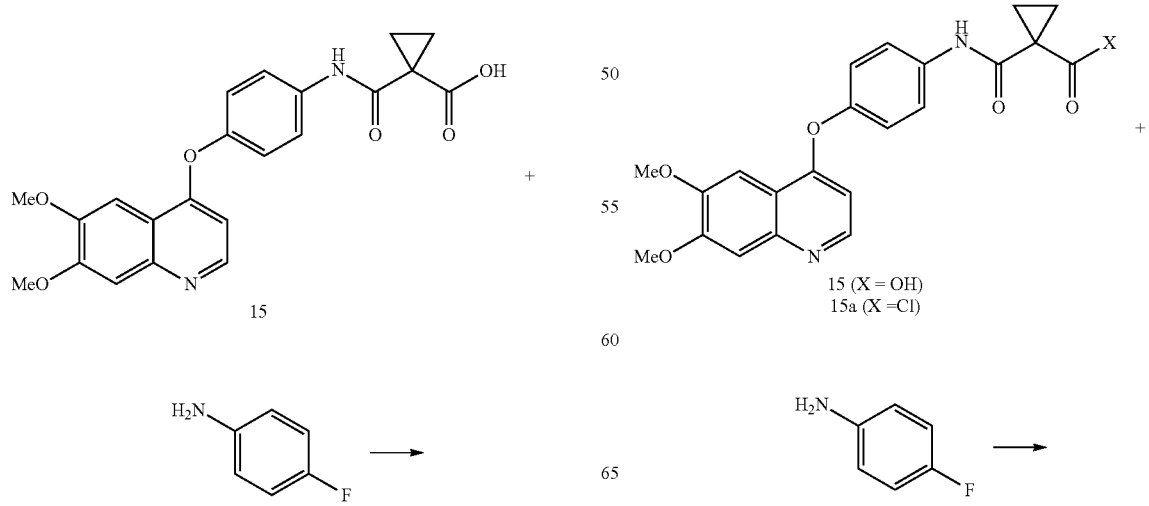

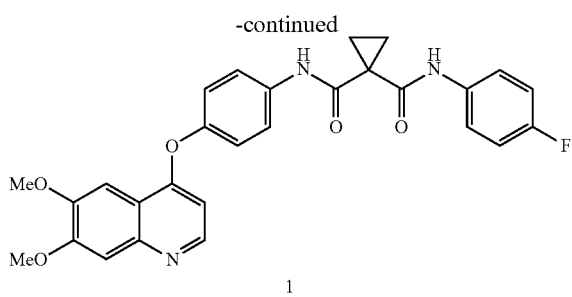

To a mixture of the carboxylic acid (15, 123 mg, 0.30 mmol), THF (1.0 mL), and DMF (5 μL) was added oxalyl chloride (38 mg; 0.30 mmol) dropwise at room temperature. After 15 min, the acid chloride (15a) slurry was added to another flask containing a stirred suspension of 4-fluoroaniline (37 mg, 0.33 mmol), $K_2CO_3$ (104 mg, 0.75 mmol), in THF (1.0 mL) and water (0.5 mL) over approximately 2 min. After 45 min, the lower aqueous layer was removed. The upper organic layer was concentrated in vacuo and purified by column chromatography to give the desired product 1 (108 mg, 72% yield). LC/MS: Calcd for [M+H]+ 502.2. found 502.2. Anal. HPLC (10 min gradient): 99% purity, 6.62 min.

Example 8. Synthesis of 4-nitro-N,N,N-trimethylanilinium trifluoromethanesulfonate (18)

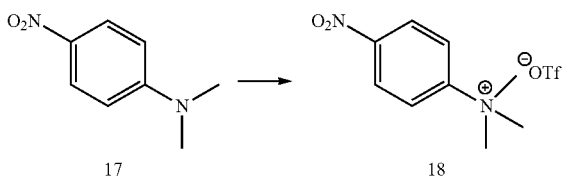

N,N-dimethyl-4-nitroaniline (17, 0.7 g, 4.0 mmol) and benzene (10 mL) were added to a nitrogen-purged flask equipped with a stir bar. To this stirring solution was added methyl trifluoromethanesulfonate (0.7 mL, 6.1 mmol) at ambient temperature. The reaction was then heated to 40° C. for a 24-hour period. At the conclusion of the reaction the N,N,N-trimethyl-4-nitrobenzenaminium trifluoromethanesulfonate (18, 1.0 g, 3.0 mmol, 75% yield) precipitated from solution as an orange solid. The product was filtered, washed with ether (3×20 mL) and placed in a high vacuum drying tube at 100° C. for 1 hour. LCMS $C_9H_{13}N_2O_2$ (M+) Calcd 181.10. Found 181.1; $^1H$ NMR ($d_6$-DMSO, 500 mHz) δ 8.45 (d, 2H, J=9.4 Hz); 8.26 (d, 2H, J=9.3 Hz); 3.66 (s, 12H); $^{13}C$ NMR ($d_6$-DMSO, 125 mHz) δ 151.0, 147.6, 124.9, 122.5, 56.24.

Radiochemical Synthesis

Example 9. Synthesis of K.2.2.2/K[$^{18}$F]F Complex (19)

The aqueous [$^{18}$F]-Fluoride solution (1.0 mL, 18.5 GBq/500 mCi) was purchased from P.E.T. Net® Pharmaceuticals in West Point Pa. and shipped to the site. The average delivery time at the end of bombardment was 80 minutes, and once delivered, was transferred to our remote controlled synthesis apparatus and delivered to a Sep-Pak light QMA [The Sep-Pak light QMA cartridge was pre-conditioned sequentially with 5 mL of 0.5 M potassium bicarbonate, 5 mL of deionized water, and 5 mL of MeCN before use]. Upon completion of this transfer, the aqueous [$^{18}$F]-fluoride was released from the QMA Sep-Pak by the sequential addition of potassium carbonate (15 mg/mL; 0.1 mL) followed by a mixture of potassium carbonate (30 mg/ml, 0.1 mL), 4,7,13,16,21,24-hexaoxa-1,10-diazabicyclo[8.8.8]hexacosane (Kryptofix® 2.2.2., 15 mg, 0.04 mmol) and 1.2 mL of MeCN. The solvent was evaporated under a gentle stream of nitrogen at 90° C. and vacuum. Azeotropic drying was repeated twice with 1 mL portions of acetonitrile to generate the anhydrous Kryptofix 2.2.2/K[$^{18}$F]F complex.

Example 10. Radiosynthesis of [$^{18}$F]-fluoroaniline (9a) using 4-nitro-N,N,N-trimethylanilinium trifluoromethanesulfonate (18)

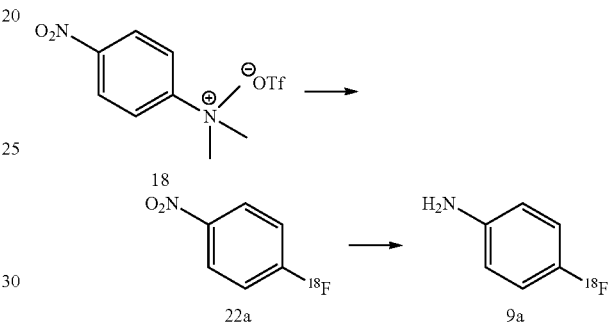

4-Nitro-N,N,N-trimethylanilinium trifluoromethanesulfonate (18) (5.0 mg, 0.02 mmol) was dissolved in 0.3 mL DMSO and added to the dried Kryptofix 2.2.2/K[$^8$F]-F salt (19). The resultant solution was heated at 120° C. for 3 minutes. After heating, the contents of this reaction vial were diluted with 10 mL of DI water. This solution was passed through three Sep-Pak cartridges that were connected in series. In the first step, the crude reaction mixture is passed through a basic alumina light cartridge followed by a Merck LiChrolut® SCX cartridge to remove unreacted K[$^{18}$F]F. In the second step, the reaction mixture is passed through a SCX Sep-Pak cartridge to remove unreacted trimethylanilinium salt (18). In the final step, the compound is passed through C-18 Sep-Pak cartridge (Waters P.N. WAT 020515, 360 mg) that was pre-conditioned with 10 mL ethanol & 10 mL DI water to remove the reaction solvent (for example, dimethyl sulfoxide). The [$^{18}$F]-1,4-fluoronitrobenzene (22a) was retained onto C-18 Plus Sep-Pak. Residual Kryptofix 2.2.2 was rinsed from the C-18 Plus Sep-Pak by an addition of 10 mL of 0.1 N HCl. [$^{18}$F]-1,4-fluoronitrobenzene was eluted from this Sep-Pak via the addition of 2 mL of anhydrous methanol. The schematic diagram showing the various steps of purification of [$^{18}$F]-1,4-fluoronitrobenzene is shown in FIG. 1. The eluted methanol solution containing [$^{18}$F]-1,4-fluoronitrobenzene was transferred into a sealed 5 mL microvial that contained palladium black (11.0 mg, 0.1 mmol), phosphorous acid (0.10 g, 1.3 mmol) and conical stir bar. The resulting solution was then heated at 60° C. for 15 minutes and then this reaction mixture was filtered through a 25 mm, 0.45 μm nylon membrane syringe filter to remove any palladium black. The remaining solution was diluted with 25 mL of 1 N NaOH and transferred to the Merck EN Sep-Pak (this Sep-Pak was pre-activated with 5 mL of EtOH followed by 10 mL 1 N NaOH). 2 mL of DCM was added to the EN Sep-Pak to elute the [$^{18}$F]-4-fluoroaniline (9a) into the 5 mL microvial microwave station. The volume of DCM was reduced with a gentle stream of nitrogen and heated at 40° C. until approximately 0.2 mL of this solution remained. To this reaction mixture was added 0.5 mL DMF and this mixture was azeotropic dried twice with 1 mL portions of DCM to generate the anhydrous [$^8$F]-fluoroaniline (9a) in DMF. Attempts to reduce the volume of (9a) below 0.2 mL resulted in significant volitization of the product and were subsequently avoided.

Example 11. Radiosynthesis of [$^{18}$F]-Cabozantinib, Cyclopropane-1,1-dicarboxylic acid [4-(6,7-dimethoxy-quinolin-4-yloxy)-phenyl]-amide(4-[$^{18}$F]-fluoro-phenyl)amide) (1b)

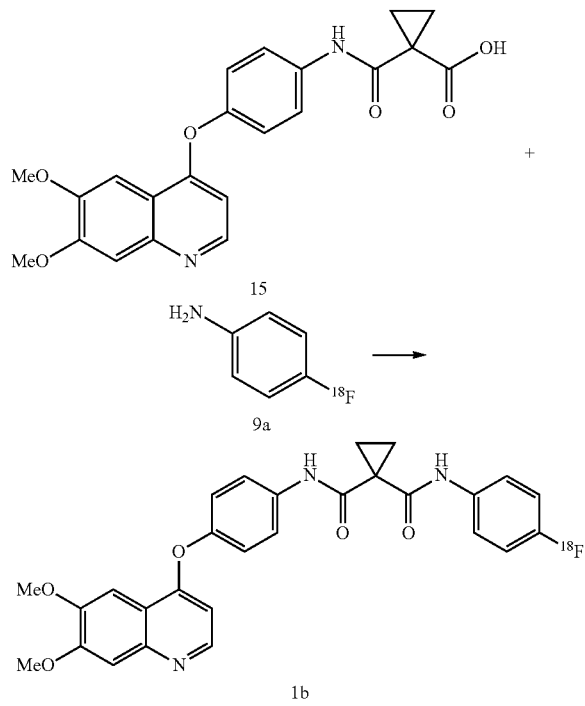

Figure 2:
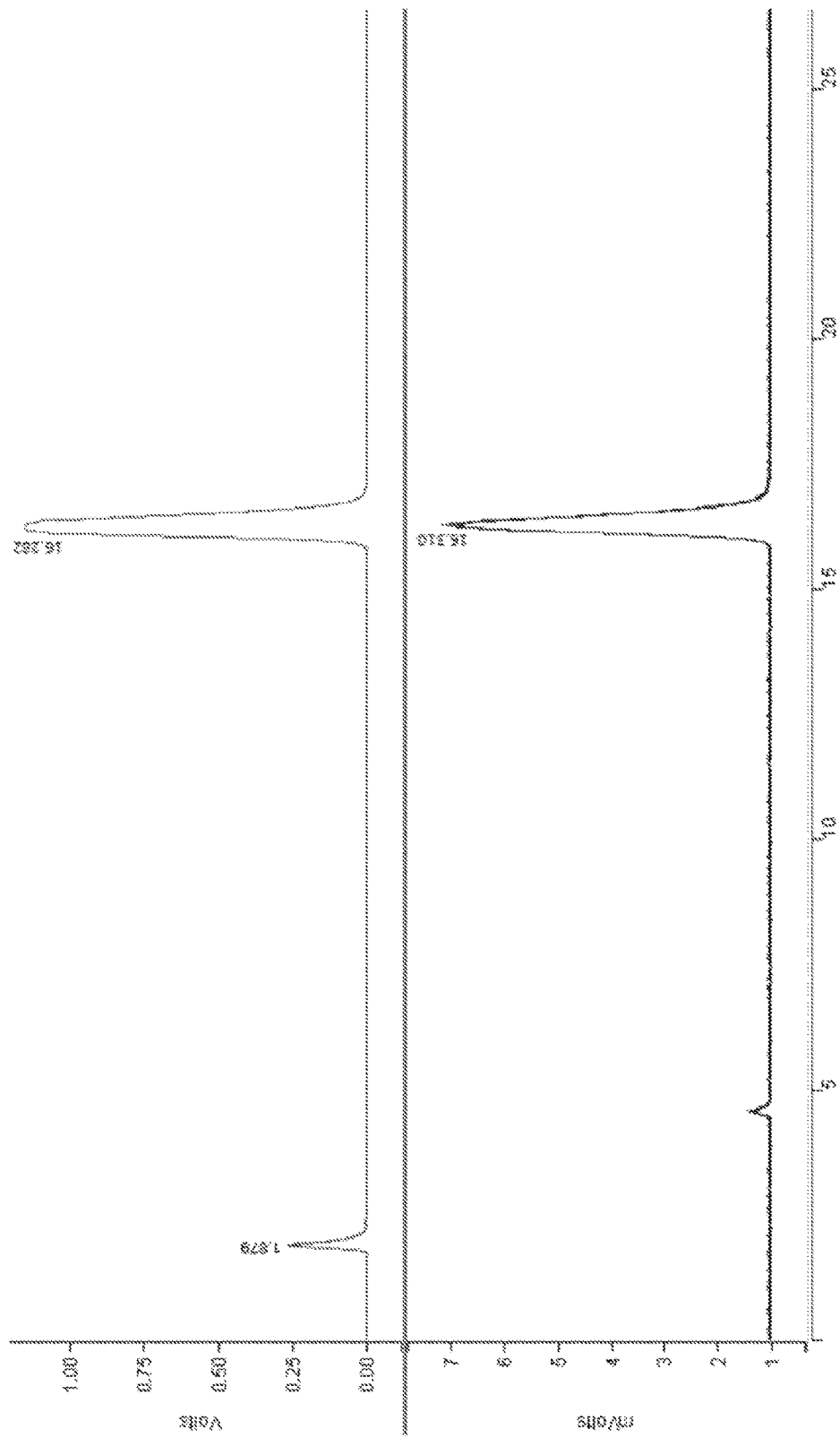
FIG. 2 depicts a radio-HPLC chromatogram showing co-elution of [$^{18}$F]-Cabozantinib co-injected with non-radioactive reference standard.

A mixture of 1-(4-(6,7-dimethoxyquinolin-3-yloxy)phenylcarbamoyl)cyclopropanecarboxylic acid (10 mg, 0.024 mmol, 15), 2-(3H-[1,2,3]triazolo[4,5-b]pyridine-3-yl)-1,1,3,3-tetramethylisouronium hexafluorophosphate(V) (19 mg, 0.05 mmol), and N-ethyl-N-isopropylpropan-2-amine (20 μL, 0.1 mmol) were dissolved in 0.3 mL DMF and added to the 5 mL microvial containing [$^{18}$F]-4-fluoroaniline (9a). The reaction was then heated with the microwave apparatus at 85° C. with 10-20 W for 20 minutes. After this period of heating, 5.0 mL of 25 mM potassium phosphate dibasic solution, 1.5 mL of acetonitrile were added to the microvial and this solution was loaded onto a 9.4×250 mm, 5 micron Zorbax SB-C18 column using an isocratic mobile phase of 45% acetonitrile and 65% 25 mM potassium phosphate dibasic solution (pH 9.0). The UV detector was set at 254 nm. [$^{18}$F]-Cabozantinib was isolated at the 30 minute mark using these conditions. This sample was then diluted with 25 mL of 25 mM potassium phosphate dibasic and the entire sample was loaded onto a Waters Sep-Pak C18 Plus Short Cartridge, 360 mg Sorbent per Cartridge, 55-105 μm Particle Size (part number WAT020515) which was preactivated with 5 ml of ethanol, followed by 10 mL of DI water. After the entire solution was loaded onto the C18 Sep-Pak the final product was released with 0.5 mL of ethanol to give 902.8 MBq/24.4 mCi of [$^{18}$F]-Cabozantinib, cyclopropane-1,1-dicarboxylic acid [4-(6,7-dimethoxy-quinolin-4-yloxy)-phenyl]-amide(4-[$^{18}$F]-fluoro-phenyl)amide, 1b. This peak was confirmed to be [$^{18}$F]-Cabozantinib 1b via co-injection of reference standard on analytical HPLC and radiochemical purity was >99% (FIG. 2). In system A, [$^{18}$F]-Cabozantinib 1b co-eluted with the non-radioactive standard 1 and had a $R_f$ of 10.2-10.5 min and in system B, [$^{18}$F]-Cabozantinib 1b co-eluted with the non-radioactive standard 1 and had a $R_f$ of 14.5-14.8 min. The specific activity was measured using a Zorbax SB C18 HPLC column using an isocratic mobile phase of 50% acetonitrile and 50% 25 mM potassium phosphate dibasic in distilled water. The UV was monitored at 254 nM and the flow rate was 1 mL/min, generating a back pressure of 1100 PSI. The specific activity using this method was measured against a 6 point calibration curve and determined to be 42.2+/-10 GBq/μmol (1.14+/-0.2 Ci/μmol).

Example 12. Radiosynthesis [$^{18}$F]-Cabozantinib: Variation of Microwave Reaction Conditions The coupling reaction as described in Example 11 was conducted by varying microwave heating at various wattages and solvents. The results are shown in Table 1. A significant amount of precursor decomposition was noticed when the reactions conducted at powers above 20 W. An increase in the isolated amount of [$^{18}$F]-Cabozantinib 1b was seen using DMF as the reaction solvent and decreased when DMSO, THF, or a mixture of DMF/DMSO. [$^{18}$F]-Cabozantinib 1b was isolated (903 MBq+/−120 MBq; 24.4 mCi+/-3.2 mCi, n=10) in radiochemical yields (13%, decay corrected) after HPLC purification in high radiochemical purity (>99%). The specific activity was 42.2 GBq/μmol+/- 7.5 GBq/μmol (1.14 Ci/μmol+/−0.2 Ci/μmol). The retention time of this radioactive product was confirmed by co-injection of the non-radioactive standard Cabozantinib as shown in FIG. 2, using two separate analytical HPLC systems (Systems A and B).

TABLE 1

Investigation of [$^{18}$F]-Cabozantinib using microwave heating

| Experiment No. | Microwave power | Time | Solvent | Radiochemical yield of [$^{18}$F]-Cabozantinib (1A) (decay corrected) |
|---|---|---|---|---|
| 1 | 10 W | 20 min. | DMF:DMSO | 1.1% |
| 2 | 20 W | 20 min | DMF:DMSO | 1.3% |
| 3 | 20 W | 20 min | DMF | 13.8% |
| 4 | 20 W | 20 min | DMSO | 0.0% |
| 5 | 50 W* | 10 min | DMF:DMSO | 0.7% |
| 6 | 10 W | 20 min | THF | 0.0% |

*At 50 W, precursor decomposition was observed.

Example 13. Radiometabolite Analysis in Plasma 7.4-6.4 MBq (0.2-0.17 mCi) of [$^{18}$F]-Cabozantinib was injected into athymic BALB/C mice (Harlan) and these animals were maintained on 1-2% isofluorane during injection, tracer uptake, and blood sampling. 100 μL aliquots samples of blood were collected in lithium heparin coated tubes either from the contralateral tail vein or the retroorbital plexus at 15 and 60 minutes after [$^{18}$F]-Cabozantinib injection. These samples were centrifuged for 10 minutes at 10,000 rpm for plasma separation at 4° C., washed with equal amounts of methanol. 10 µL of the methanol extract of plasma was co-spotted with non-radioactive reference compound onto and across the TLC plates (Silica Gel GHLF; Scored 2.5×10 cm; 250 microns), blow-dried with warm air and developed in a TLC chamber. The TLC solution used in this study was 8% methanol in dichloromethane which gave a $R_f$ of approximately 0.55. After the development was completed, the TLC plate was placed onto the radio-TLC scanner (Bioscan AR2000), which scanned the TLC plate for 15 minutes. The peak areas were calculated to give the metabolite profile of [$^{18}$F]-Cabozantinib.

Example 14. PET Imaging in Mice

Rodent imaging experiments were performed on a dedicated small animal microPET® F120™ scanner (Siemens Preclinical Solutions, Knoxville, Tenn.). Both static and dynamic PET imaging studies were conducted on athymic BALB/C mice (Harlan) and stereotactically implanted U87 tumor cells. The mice were administered about 6.4-7.4 MBq (0.17-0.2 mCi) of [$^{18}$F]-Cabozantinib via the tail vein. The mice were anesthetized (2% isofluorane in $O_2$ at a flow rate of 1 mL/min) during tracer injection and throughout the imaging period. After injection, each mouse was laid in the microPET scanner. A 10 minutes transmission scan was acquired using a $^{57}$Co point source prior to either the 2 hour dynamic scan or the 45 min static scan starting at about 15 minutes after injection. Mice were visually monitored for breathing, and a heating pad was used to maintain body temperature throughout the entire procedure. PET data were reconstructed using an OSEM 2D algorithm into a 128×128×95 image matrix (resulting in final voxel dimensions of 0.79×0.79×0.8 mm). Dead time, decay correction, attenuation correction, and normalization were applied to all PET data. Data were analyzed by manually drawing standardized volumes of interest using the Siemens ASIPro VM software package version 6.6.

Example 15. In Vivo PET Imaging of [$^{18}$F]-Cabozantinib (1b)

Dynamic PET acquisitions were carried out on 3 mice with orthotopically implanted U87 tumor cells 19 days after cells were stereotactically implanted and 2 tumor-free animals for a 2 hour period. As can been seen in FIG. 3, the summed PET images of the tumor-free control mice after injection of 0.62 MBq (0.17 mCi) of [$^{18}$F]-Cabozantinib, shows little to no [$^{18}$F]-Cabozantinib (SUV mean 0.19) uptake in the brain of these control animals. A significant increase in [$^{18}$F]-Cabozantinib uptake was observed in the PET image of the orthotopically implanted U87 mice (SUV mean 0.50 (n=3)) giving a high 2.4-2.6 tumor: brain ratio measured in these animals. MRI confirmed the location of these tumors. In all 3 animals with orthotopically implanted U87 tumor cells, visualization of the tumor could be observed with this tracer. These results suggest that this tracer does not cross the blood brain barrier in tumor-free mice and has significant uptake in U87 orthopically implanted in mice. From time activity curves, a steady accumulation of the tracer in the tumor area can be observed over the 2 hour period, with a maximal tumor uptake 60 minutes post injection.

Figure 3:
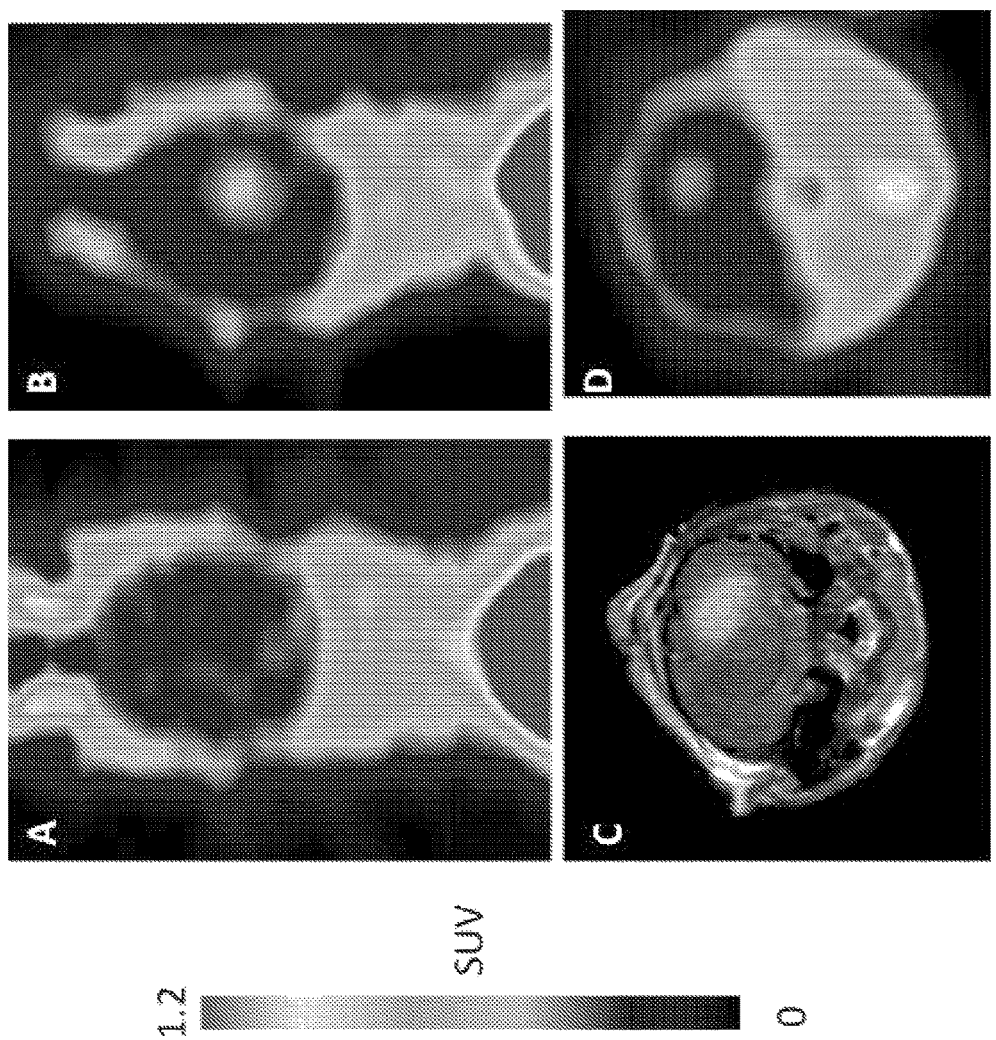
FIG. 3 depicts Positron Emission Tomography (PET) images of mice injected with [$^{18}$F]-Cabozantinib.

FIG. 3 depicts Positron Emission Tomography (PET) images of mice injected with [$^{18}$F]-Cabozantinib. Frame shows PET image of control mice, i.e., non-tumor bearing. Frame B shows PET image of mice with stereotactically implanted U87 tumor cells. Images are summed frames over 15-45 post injection of a 6.3 MBq (0.17 mCi) of [$^{18}$F]-Cabozantinib. A tumor:brain ratio, which is the ratio of the amount of [$^{18}$F]-Cabozantinib in the tumor compared to the amount of [$^{18}$F]-Cabozantinib in the brain in non-tumor regions, of 2.6 to 2.8 was measured for U87 stereotactically implanted tumor cells. Frame C shows MRI image of the same stereotatically implanted U87 tumor bearing mouse as shown in Frame B. Frame D shows PET image in the same animal, in the same view as MRI (Frame C) to confirm tumor location and PET tracer uptake in the tumor region.

Example 16. Stereotactic Intracranial Surgical Procedures

All animal procedures were done in accordance with established policy and protocols. Athymic BALB/C mice (Harlan) were anesthetized (2% isofluorane in $O_2$ at a flow rate of 1 L/min) and positioned in a stereotaxic atlas prior to surgery. A midline cranial incision was made and bregma located. From bregma, the coordinates 2 mm lateral×2 mm posterior were used, and a small bore hole was made with a dental drill. Using a Hamilton syringe (30 g) inserted to a depth of 3 mm, 2.5×10$^5$ U87 cells (ATCC) in 10 µL of RPMI were injected over a 3 minute period. Bone wax (Ethicon) was used to seal the burr hole followed by Veterinary Tissue Adhesive (3M) to close the incision. Mice were recovered from anesthesia, observed for any signs of pains or distress, and if necessary, provided appropriate veterinary care. After 7 days, mice were initiated on imaging protocols to monitor disease progression Example 17. Biodistribution Groups of athymic BALB/C mice were implanted with a subcutaneous U87 tumor cells (N=6) were anesthetized, and administered [$^{18}$F]-Cabozantinib (4-10 MBq) in 100 µL 10% ethanol in saline. After acute sedation with isofluorane (2%) animals were sacrificed by decapitation at 15 and 60 min following tracer injection. Blood samples were collected and portions of the liver, kidneys, heart, lungs, muscles, stomach, large intestine, small intestine, bladder, spleen, brain and femur were dissected and weighed. Radioactivity of each sample was measured using a gamma counter (1480 Wizard™ 3 Automatic Gamma Counter, PerkinElmer). Decay-corrected radioactivity concentrations were calculated as percentage of injected dose per gram tissue (% ID/g).

Biodistribution Data and In Vivo Metabolism of [$^{18}$F]-Cabozantinib

Example 18. In Vivo Metabolism of [$^{18}$F]-Cabozantinib (1b)

Figure 4:
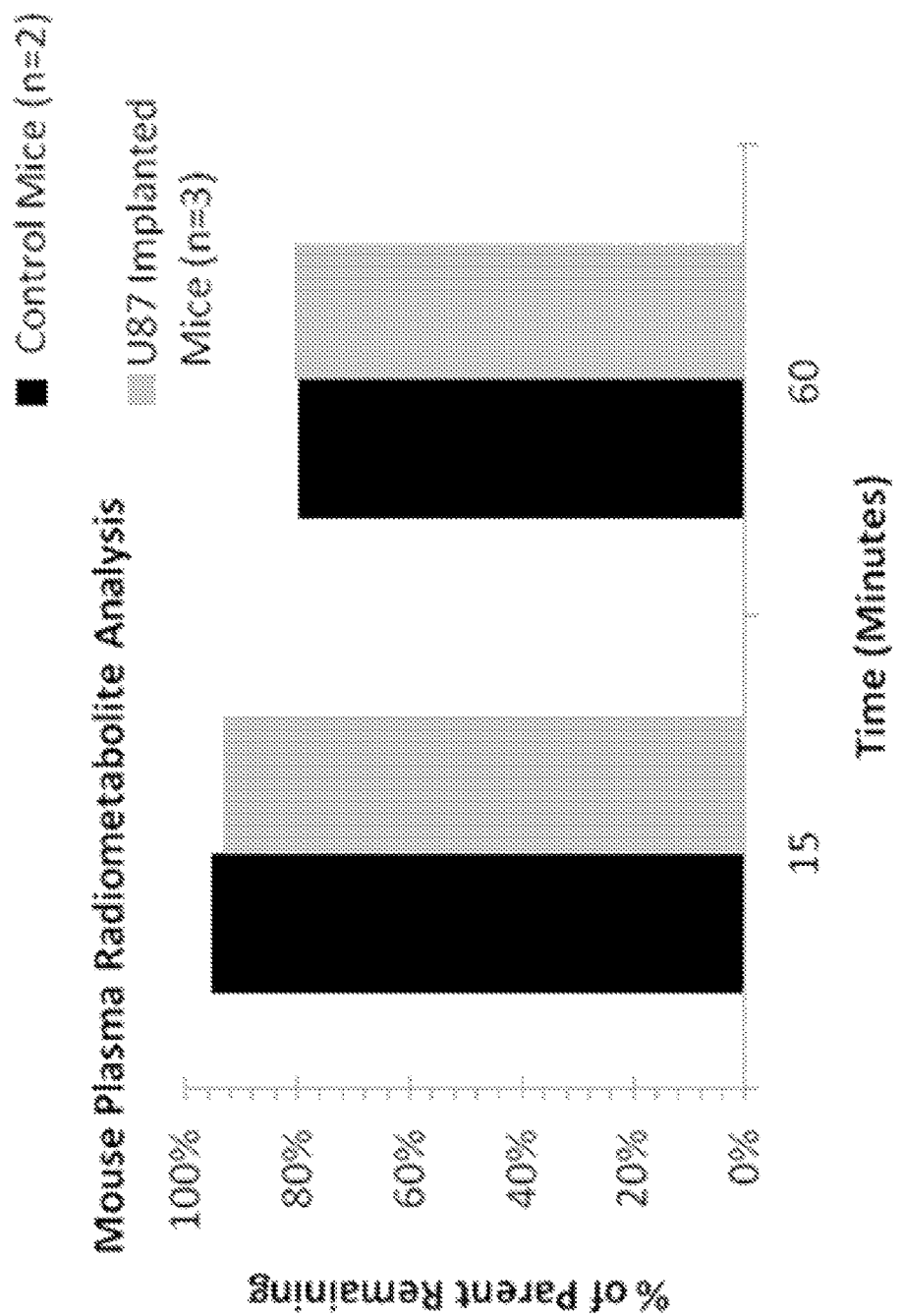
FIG. 4 depicts the radiometabolite analysis of [$^{18}$F]-Cabozantinib in mouse plasma.

The results of the in vivo stability of [$^{18}$F]-Cabozantinib are summarized in FIG. 4. [$^{18}$F]-Cabozantinib was extracted in the plasma samples taken from mice with no significant differences in metabolism of this tracer in tumored or wild type mice. 10 µL of methanol extract of mouse plasma was co-spotted with non-radioactive reference compound onto and across the TLC plates, which were blow-dried with warm air and developed in TLC chamber. The TLC solution used in this study is 8% methanol in dichloromethane which gave a $R_f$~0.55. After the development was completed, the TLC plate was placed onto the radio-TLC scanner (Bioscan AR2000), which scanned the TLC plate for 15 minutes. The peak areas were calculated to give the metabolite profile of [$^{18}$F]-Cabozantinib. The content of the extracted radioactivity was analyzed on TLC and showed that over 80% of this tracer remained intact over the time course of this study. Only one radiometabolite was seen in this analysis and was more polar than its parent suggesting that [$^{18}$F]-Cabozantinib is stable in vivo. The biodistribution of [$^{18}$F]-Cabozantinib in mice was investigated in both through radioactivity assay of postmortem mouse tissues harvested on completion of the imaging studies at 15 and 60 minutes after injection (n=6).

Figure 5:
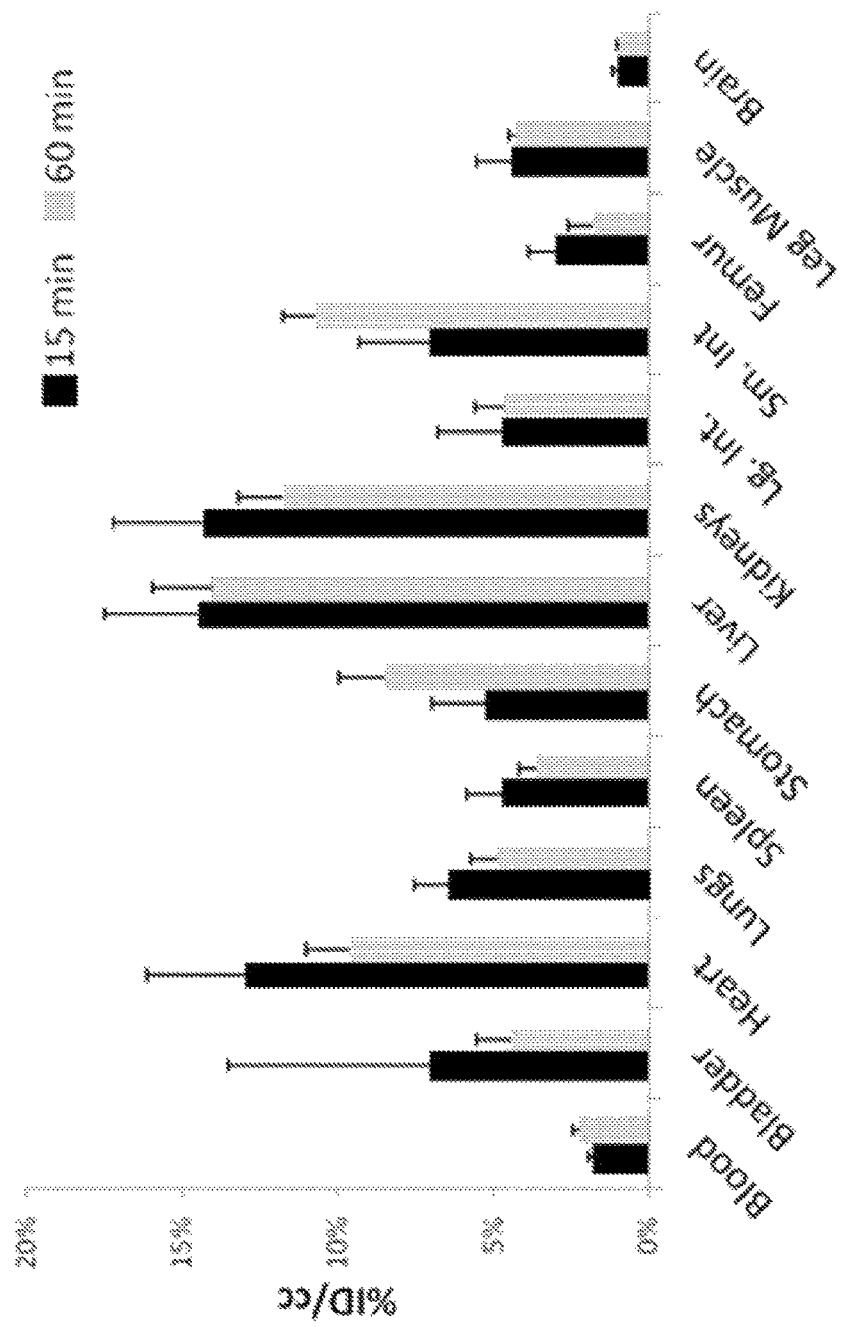
FIG. 5 depicts the biodistribution analysis of [$^{18}$F]-Cabozantinib in mice.

FIG. 5 depicts biodistribution analysis of [$^{18}$F]-Cabozantinib in mice. The bar graph represents the biodistribution (% ID/g) of [$^{18}$F]-Cabozantinib in mice (n=6) at 15 minutes post injection (blue) and 60 minutes post injection (red). At the 15 minute mark after injection, the highest tracer uptake was found in the liver (14.4±3.1% ID/g), followed by the kidneys (14.2±3.0% ID/g), heart (12.9±3.2% ID/g), bladder (7.1 f 6.5% ID/g), small intestines (7.0±2.4% ID/g), lungs (6.5±1.1% ID/g, stomach (5.2±1.7% ID/g), spleen (4.7±1.2% ID/g), large intestines (4.7±2.1% ID/g), femur (2.9±1.0% ID/g) muscles (4.4±1.1% ID/g), blood (1.8±0.2% ID/g), and brain (0.9±0.2% ID/g). At the 60 minutes post injection time point, the highest tracer uptake was found in the liver (14.0±1.9% ID/g), followed by the kidneys (11.7±1.5% ID/g), small intestines (10.7±1.1% ID/g), heart (9.5±1.5% ID/g), stomach (8.4±1.5% ID/g), lungs (4.9±0.8% ID/g, bladder (4.3±1.2% ID/g), large intestines (4.6±0.9% ID/g), muscles (4.2±0.3% ID/g), spleen (3.6±0.6% ID/g), blood (2.2±0.3% ID/g), femur (1.8±0.8% ID/g) and brain (0.9±0.1% ID/g). These results suggest that a minimal amount of radioactivity was seen in the femur and fluorine locating to bone was not a significant issue with this compound and thus supporting good stability of the radiolabel. In addition, these results show that this compound did not appear to cross the blood brain barrier.

Example 19. MRI

All MRI analyses were performed on a Bruker 7.0 T/20 cm horizontal Biospec MRI system (Bruker BioSpin, Ettlingen, Germany), and a Bruker 25-mm quadrature mouse head coil was used for RF transmitting/receiving. Mice anesthesia was induced by 2% isofluorane in 100% $O_2$ for tail vein catheter preparation. Gadopentetate Dimeglumine (Gd-DTPA, Magnevist, Bayer) contrast was diluted from 0.5 M with distilled water into 0.0625 M for mouse tail vein injection at 1 mL/kg body weight. Following Magnevist injection, the mouse under anesthesia (maintained at 1-2% isofluorane in 100% $O_2$) was immediately moved into a custom-made animal holder including a nose cone and bite bar for MRI imaging. Respiration was monitored during imaging acquisition. Scout images were collected using a RARE Tripliot of the head for the localization of the orthotopic tumor. Subsequent axial images were obtained using the following parameters to cover the identified tumor: TR/TE=1000/30 ms, FOV=1.8 cm$^2$, matrix of 128$^2$, for 6 continued slices at 1 mm slice thickness. The mouse was kept in the same animal holder and carefully moved into a PET scanner for $^{18}$F-Cabozantinib 1b PET imaging. The post-Gd axial MRI images were used for co-registration with PET images.

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

The invention claimed is:

1. A method for preparing a compound of Formula 1a:

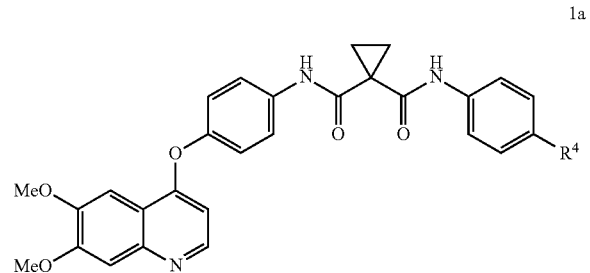

1a or pharmaceutically salt thereof wherein:
$R^4$ is $^{18}$F;
the method comprising:
i) reacting a compound of Formula 10 with a chlorinating agent to generate a compound of Formula 11:

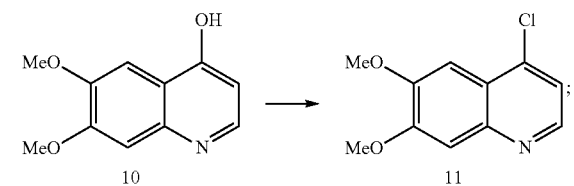 [SMILES: COc1cc2nccc(O)c2cc1OC ; COc1cc2nccc(Cl)c2cc1OC]

ii) coupling the compound of Formula 11 with a compound of Formula 23 in the presence of a base to generate a compound of Formula 12:

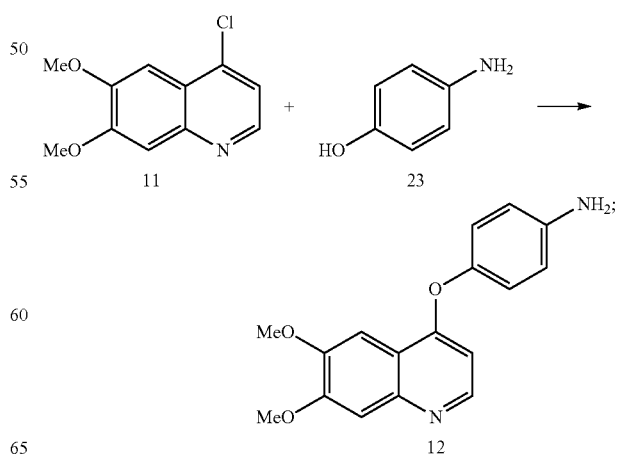

iii) coupling the compound of Formula 12 with a compound of Formula 13 in the presence of a coupling agent to generate a compound of Formula 14:

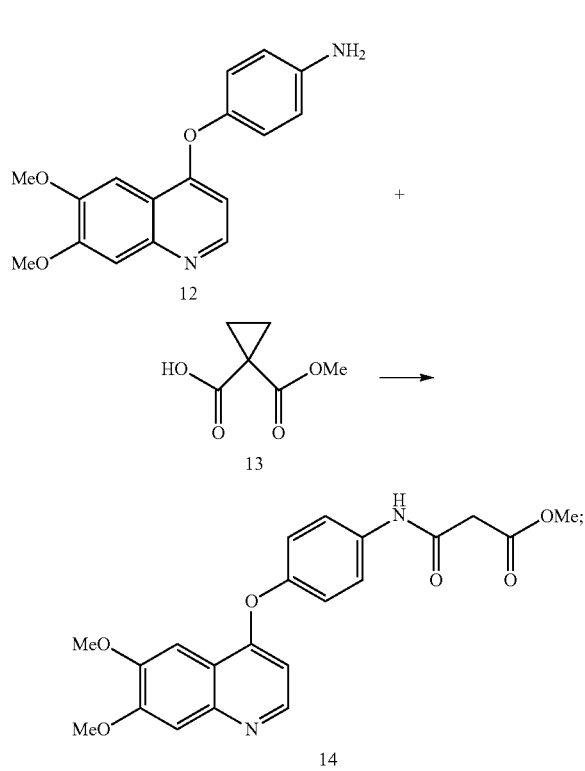

iv) saponifying the compound of Formula 14 in the presence of a base to generate a compound of Formula 15:

v) reacting the compound of Formula 15 with a halogenating reagent to generate a compound of Formula 15a:

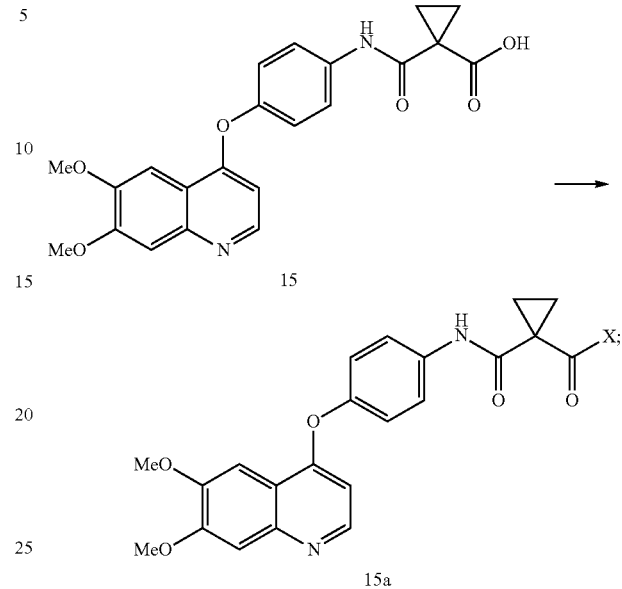

wherein X is chloro or bromo; and vi) reacting the compound of Formula 15a with a compound of Formula 9 to generate a compound of Formula 1a:

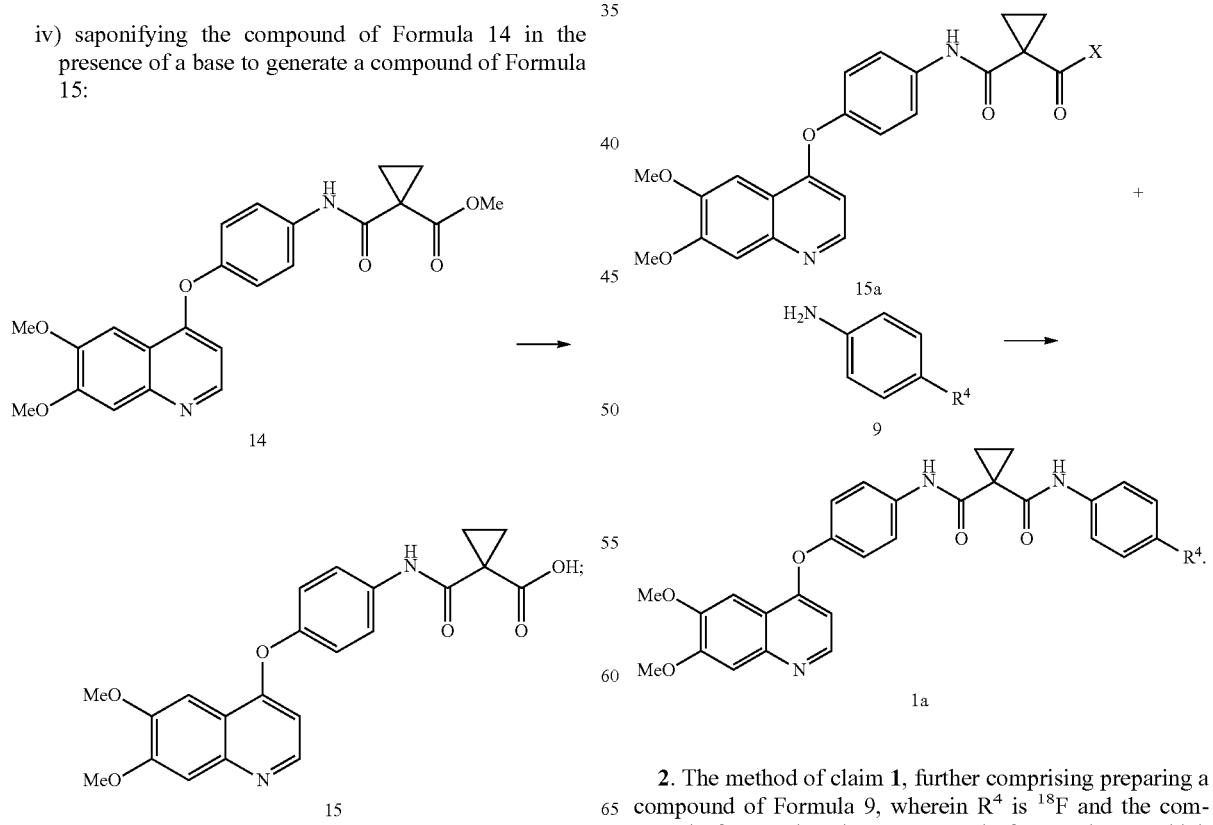

2. The method of claim 1, further comprising preparing a compound of Formula 9, wherein $R^4$ is $^{18}F$ and the compound of Formula 9 is a compound of Formula 9a, which comprises:

i) reacting a compound of Formula 18 with a fluorinating reagent to generate a compound of Formula 22a; and

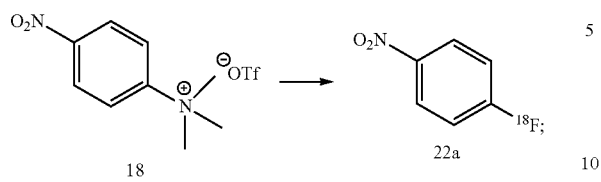

and ii) reducing the compound of Formula 22a to generate a compound of Formula 9a:

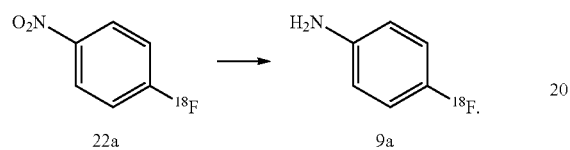

3. A method for preparing a compound of Formula 1a:

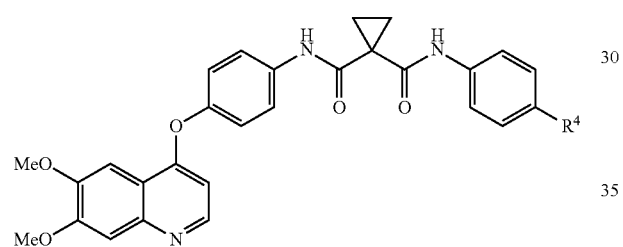

or pharmaceutically salt thereof wherein:
R⁴ is $^{18}F$;
the method comprising:
i) reacting a compound of Formula 10 with a chlorinating agent to generate a compound of Formula 11:

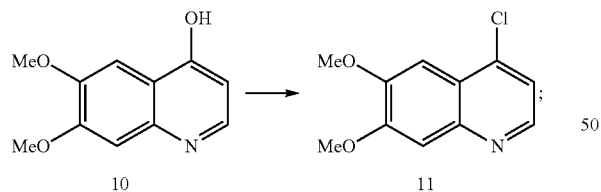

ii) coupling the compound of Formula 11 with a compound of Formula 23 in the presence of a base to generate a compound of Formula 12:

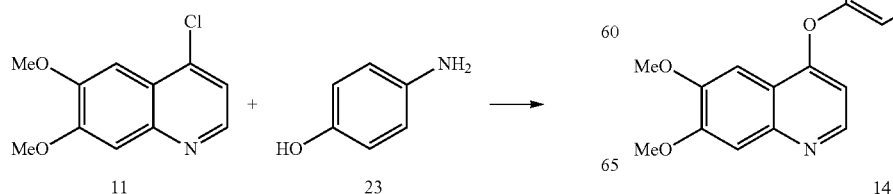

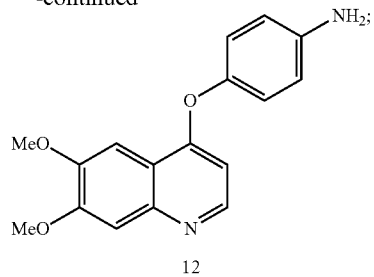

iii) coupling of the compound of Formula 12 with a compound of Formula 13 in the presence of a coupling reagent to generate a compound of Formula 14:

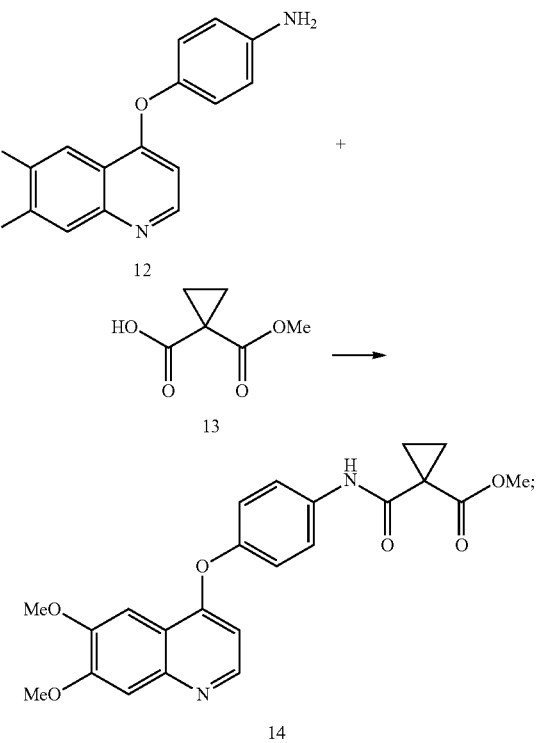

iv) saponifying the compound of Formula 14 in the presence of sodium hydroxide to generate a compound of Formula 15, wherein a solvent is used which is methanol, ethanol, isopropanol, water or a combination thereof:

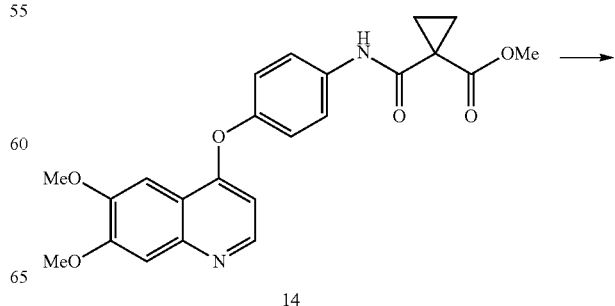

-continued

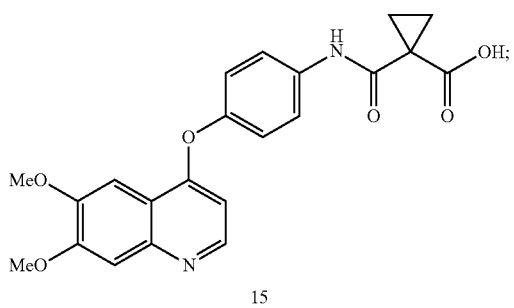

and v) coupling the compound of Formula 15 with a compound of Formula 9 in the presence of a coupling reagent to generate a compound of Formula 1a:

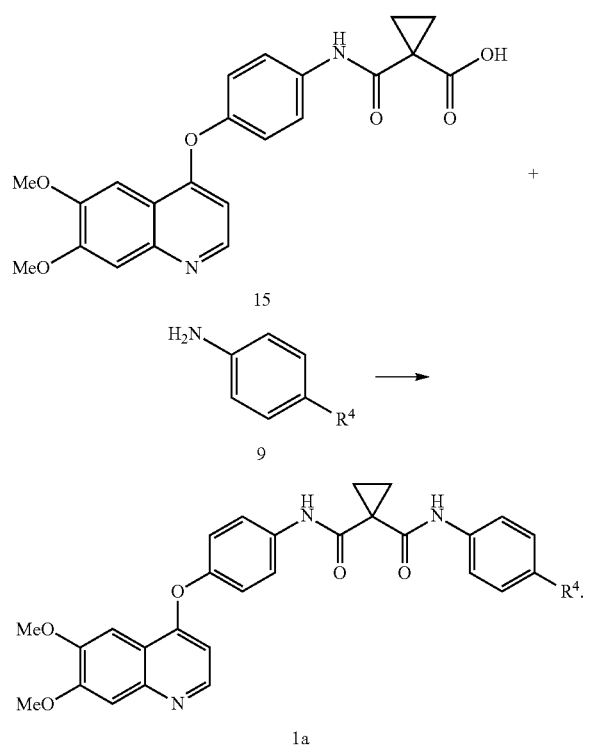

4. A method for preparing a compound of Formula 1a:

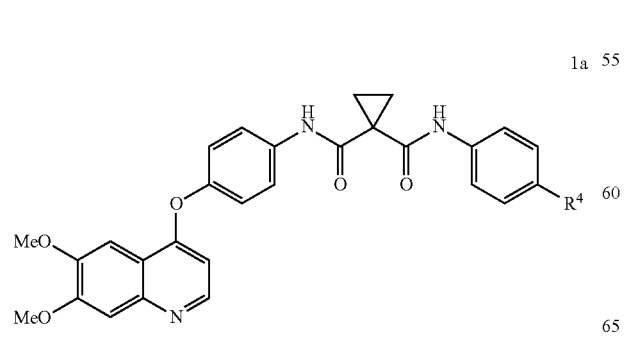

or pharmaceutically salt thereof wherein:

R⁴ is ¹⁸F;

the method comprising:

i) reacting a compound of Formula 10 with a chlorinating agent to generate a compound of Formula 11:

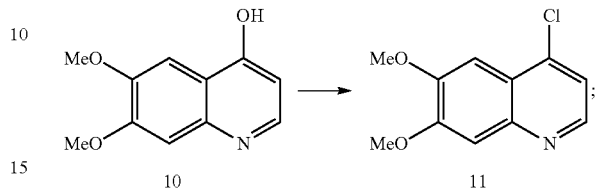

ii) coupling the compound of Formula 11 with a compound of Formula 23 in the presence of a base to generate a compound of Formula 12:

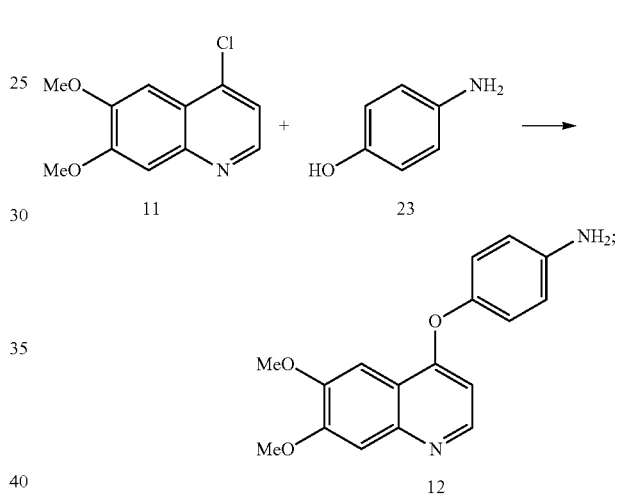

iii) coupling the compound of Formula 12 with a compound of Formula 13 in the presence of a coupling agent to generate a compound of Formula 14:

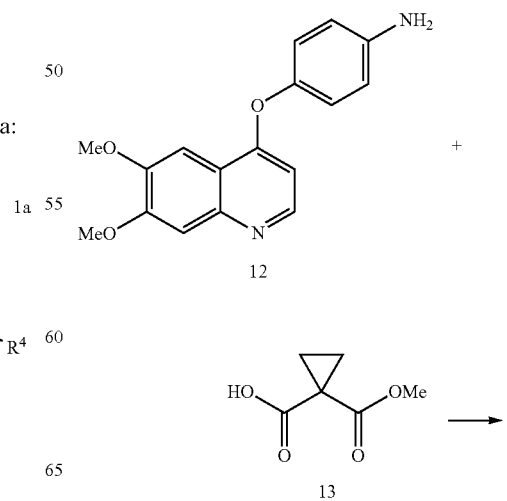

-continued

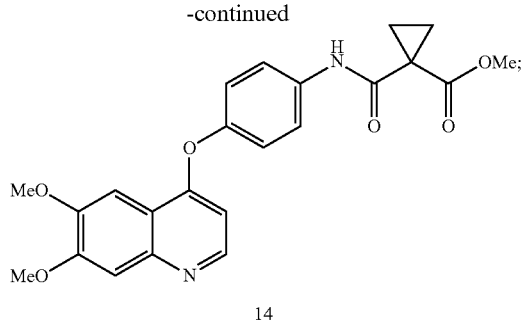
14 iv) saponifying the compound of Formula 14 in the presence of sodium hydroxide and a solvent to generate a compound of Formula 15, wherein the solvent is methanol, ethanol, isopropanol, water or a combination thereof:

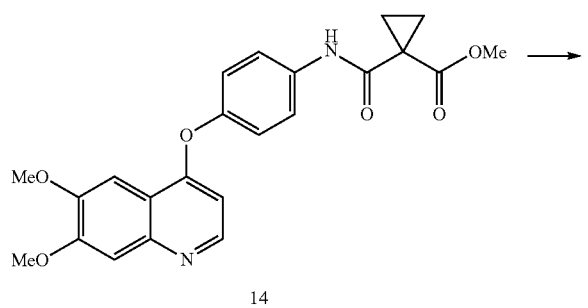
14

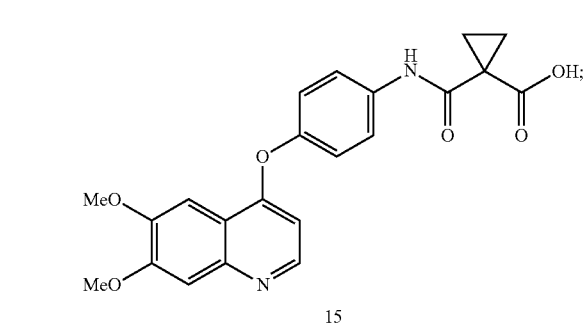
15 v) reacting the compound of Formula 15 with a halogenating reagent to generate a compound of Formula 15a:

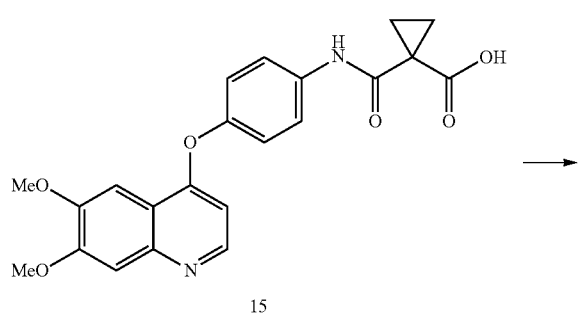
15

-continued

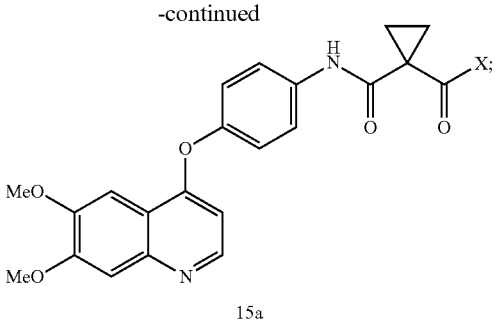
15a wherein X is chloro or bromo; and vi) reacting the compound of Formula 15a with a compound of Formula 9 to generate a compound of Formula 1a:

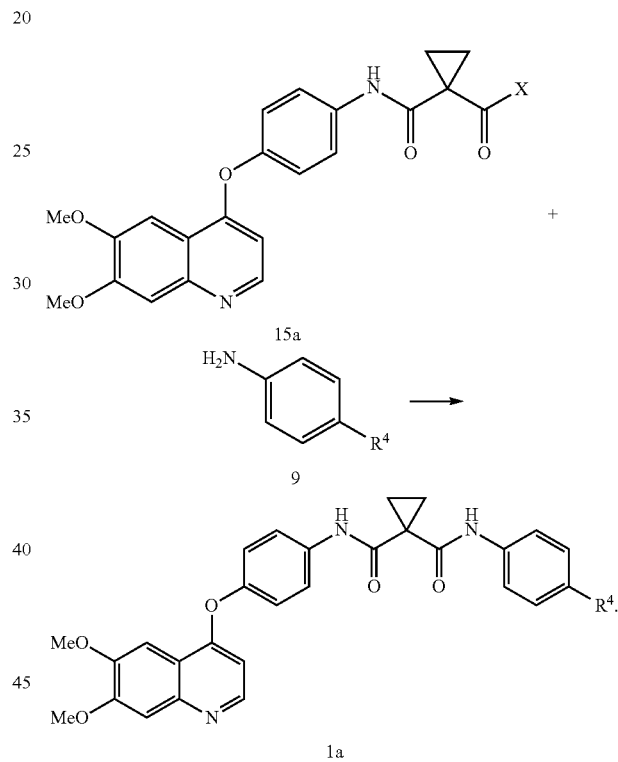

5. The method of claim 3, further comprising preparing the compound of Formula 9 wherein $R^4$ is $^{18}F$ and the compound of Formula 9 is a compound of Formula 9a, which comprises:

i) reacting a compound of Formula 18 with a fluorinating reagent to generate a compound of Formula 22a; and

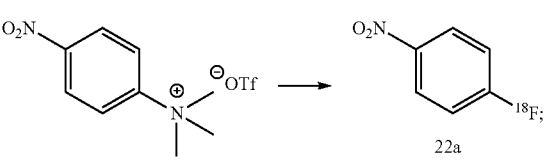

and ii) reducing the compound of Formula 22a to generate a compound of Formula 9a:

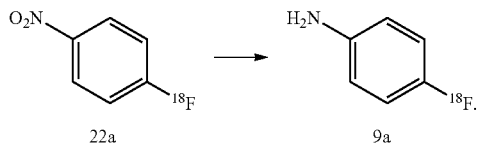

6. The method of claim 4, further comprising preparing the compound of Formula 9 wherein $R^4$ is $^{18}F$ and the compound of Formula 9 is a compound of Formula 9a, which comprises:

i) reacting a compound of Formula 18 with a fluorinating reagent to generate a compound of Formula 22a; and

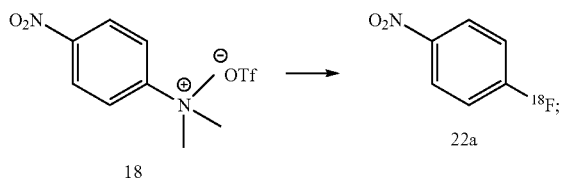

and ii) reducing the compound of Formula 22a to generate a compound of Formula 9a:

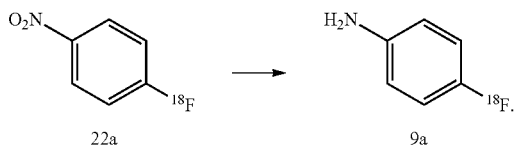

7. The method of claim 1, wherein the chlorinating agent is selected from thionyl chloride, thionyl bromide, oxalyl chloride, phosphorus pentachloride and phosphorus trichloride.

8. The method of claim 1, wherein the base in step ii) is sodium hydroxide, potassium hydroxide, lithium diisopropylamide, lithium tetramethylpiperidide, sodium tert-butoxide, potassium tert-butoxide or sodium-pentoxide.

9. The method of claim 8, wherein the base is sodium t-butoxide.

10. The method of claim 1, wherein the coupling agent in step iii) is N,N'-dicyclohexylcarbodiimide (DCC), N,N'-diisopropylcarbodiimide (DIC), 1-ethyl-3-(3-dimethylaminopropyl)carbodiimide (EDCI), hydroxybenzotriazole (HOBt), 1-hydroxy-7-azabenzotriazole (HOAt), benzotriazole-1-yl-oxytripyrrolidinophosphonium hexafluorophosphate (BOP reagent) benzotriazol-1-yl-oxytripyrrolidinophosphonium hexafluorophosphate (PyBOP), 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium tetrafluoroborate (TBTU), N,N,N',N'-tetramethyl-O-(1H-benzotriazol-1-yl)uranium hexafluorophosphate (HBTU), O-[(ethoxycarbonyl)cyanomethylenamino]-N,N,N',N'-tetramethyluronium tetrafluoroborate (TOTU), or (1-cyano-2-ethoxy-2-oxoethylidenaminooxy)dimethylamino-morpholino-carbenium hexafluorophosphate (COMU).

11. The method of claim 10, wherein the coupling agent is N,N'-diisopropylcarbodiimide.

12. The method of claim 1, wherein the base in step iv) is selected from sodium hydroxide, lithium hydroxide, caesium hydroxide, and potassium hydroxide.

13. The method of claim 12, wherein the base is sodium hydroxide.

14. The method of claim 1, wherein the halogenating agent is thionyl chloride, thionyl bromide, oxalyl chloride, phosphorus pentachloride or phosphorus trichloride.

15. The method of claim 14, wherein the halogenating agent is thionyl chloride or oxalyl chloride.

16. The method of claim 1, wherein step vi) is carried out in the presence of a base.

17. The method of claim 16, wherein the base is potassium carbonate, sodium carbonate, sodium bicarbonate, triethyl amine (TEA), diisopropyl ethyl amine (DIPEA), pyridine, N,N-dimethylamino-4-pyridine (DMAP) or N-methylmorpholine (NMO).

18. The method of claim 16, wherein the base is diisopropyl ethyl amine.

19. The method of claim 2, wherein the fluorinating reagent is K[$^{18}F$] bound to a cryptand, wherein cryptand is 1,10-diaza-4,7,13,16,21,24-hexaoxa-1,10-diazabicyclo[8.8.8]hexacosane (Kryptofix® 2.2.2. or Kryptofix 2.2.2 or Kryptofix 222).

20. The method of claim 2, wherein the reducing is carried out in the presence of a metal catalyst, an acid and hydrogen.

21. The method of claim 19, wherein the reducing is carried out in the presence of palladium, palladium black, platinum, rhodium, or nickel catalyst.

* * * * *